United States Patent
Dandiker et al.

(10) Patent No.: US 11,202,760 B2
(45) Date of Patent: Dec. 21, 2021

(54) COMPOSITIONS OF MIDODRINE AND METHODS OF USING THE SAME

(71) Applicant: XENAMED CORP., St. Paul, MN (US)

(72) Inventors: Yogesh Dandiker, Edina, MN (US); Maulik Panchal, Maple Grove, MN (US); Xiao Yu, Maple Grove, MN (US)

(73) Assignee: XENAMED CORP., St. Paul, MN (US)

( * ) Notice: Subject to any disclaimer, the term of this patent is extended or adjusted under 35 U.S.C. 154(b) by 0 days.

(21) Appl. No.: 16/338,317

(22) PCT Filed: Sep. 29, 2017

(86) PCT No.: PCT/US2017/054323
§ 371 (c)(1),
(2) Date: Mar. 29, 2019

(87) PCT Pub. No.: WO2018/064490
PCT Pub. Date: Apr. 5, 2018

(65) Prior Publication Data
US 2020/0022919 A1    Jan. 23, 2020

Related U.S. Application Data

(60) Provisional application No. 62/402,844, filed on Sep. 30, 2016.

(51) Int. Cl.
| | | |
|---|---|---|
| *A61K 9/20* | (2006.01) | |
| *A61K 9/00* | (2006.01) | |
| *A61K 9/28* | (2006.01) | |
| *A61K 31/165* | (2006.01) | |

(52) U.S. Cl.
CPC .......... *A61K 9/2054* (2013.01); *A61K 9/0056* (2013.01); *A61K 9/2031* (2013.01); *A61K 9/2059* (2013.01); *A61K 9/2086* (2013.01); *A61K 9/28* (2013.01); *A61K 31/165* (2013.01)

(58) Field of Classification Search
CPC .................................................. A61K 9/0056
See application file for complete search history.

(56) References Cited

U.S. PATENT DOCUMENTS

| | | |
|---|---|---|
| 3,131,068 A | 4/1964 | Martin et al. |
| 5,128,144 A | 7/1992 | Korsatko-Wabnegg et al. |
| 5,360,822 A | 11/1994 | Morino et al. |
| 6,761,904 B2 | 7/2004 | Bertelsen et al. |
| 7,070,803 B2 | 7/2006 | Skinhoj et al. |
| 8,263,125 B2 | 9/2012 | Vaya et al. |
| 8,268,352 B2 | 9/2012 | Vaya et al. |
| 9,314,999 B2 | 4/2016 | Cloutier et al. |
| 9,433,592 B2 | 9/2016 | Rosa-Calatrava et al. |
| 9,457,059 B2 | 10/2016 | Tidmarsh |
| 2002/0147232 A1 | 10/2002 | Sundgreen et al. |
| 2011/0076511 A1 | 3/2011 | Paolilli et al. |
| 2013/0287823 A1 | 10/2013 | Udagawa et al. |
| 2014/0154313 A1 | 6/2014 | Counts et al. |

OTHER PUBLICATIONS

International Search Report and Written opinion for International Application No. PCT/US2017/054323, United States Patent Office, United States, dated Dec. 14, 2017, 8 pages.
Hou, S., and Davis, M., "Poster 303 Bladder Distension Associated with Hypotension in a Patient with Tetraplegia after Spinal Cord Injury: A Case Report," *PM&R* 8(9S):S258-S259, American Academy of Physical Medicine and Rehabilitation, United States (Sep. 2016).
Korsatko-Wabnegg, B., *et al.*, "A study on the formulation of press-coated tablets with 'delayed-release' effect using poly-D(—)-3-hydroxybutyric acid as a coating material," *Pharmazie* 46(3):204-206, VEB Verlag Volk und Gesundheit, Germany (Mar. 1991).

*Primary Examiner* — Gina C Justice
(74) *Attorney, Agent, or Firm* — Sterne, Kessler, Goldstein & Fox P.L.L.C.

(57) ABSTRACT

This disclosure provides pharmaceutical compositions comprising midodrine, a pharmaceutically acceptable salt thereof, desglymidodrine, a pharmaceutically acceptable salt thereof, or a combination therefore that can be administered to a human subject in need thereof in a supine position. The disclosure also provides pharmaceutical compositions which can be administered once-a-day. This disclosure further provides pharmaceutical compositions comprising an extended release composition and providing a delayed release period between about 30 min to about 12 hours.

20 Claims, 9 Drawing Sheets

COMPOSITIONS OF MIDODRINE AND METHODS OF USING THE SAME

CROSS-REFERENCE TO RELATED APPLICATIONS

This application claims priority to U.S. Provisional Patent Application No. 62/402,844, filed on Sep. 30, 2016, which is incorporated by reference herein in its entirety.

FIELD

The present disclosure relates to pharmaceutical compositions of midodrine, a pharmaceutically acceptable salt of midodrine, or its active metabolite desglymidodrine or a pharmaceutically acceptable salt of desglymidodrine, or combinations thereof suitable for administration in a supine position.

BACKGROUND

Orthostatic hypotension (also referred to as postural hypotension) is a form of low blood pressure in which a person's blood pressure falls when suddenly standing up or stretching. It is caused primarily by gravity-induced blood-pooling in the lower extremities, which in turn compromises venous return, resulting in decreased cardiac output and subsequent lowering of arterial pressure.

Midodrine hydrochloride (also referred to as midodrine HCl) is a peripheral selective alpha-1-adrenergic agonist and is indicated for the treatment of orthostatic hypotension. It significantly increases standing systolic blood pressure and improves symptoms in patients with neurogenic orthostatic hypotension. Midodrine hydrochloride has the chemical name (±)-2-amino-N-[2-(2,5-dimethoxyphenyl)-2-hydroxyethyl]acetamide monohydrochloride, and the structural formula as shown below:

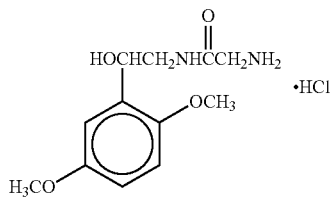

Midodrine hydrochloride is an odorless, white, crystalline powder and it is soluble in water. Midodrine hydrochloride is a prodrug which upon oral administration, is rapidly absorbed and converts to its active metabolite desglymidodrine. The absolute bioavailability of midodrine (measured as desglymidodrine) is 93%. Due to its water solubility and high permeability, midodrine hydrochloride is classified as a BCS Class I drug.

Currently within the U.S., midodrine hydrochloride is only available as an immediate release tablet. It is available in three strengths i.e., 2.5 mg, 5 mg and 10 mg. The U.S. FDA recommended a dosing of midodrine hydrochloride up to 10 mg three times a day. The tablets are to be taken at approximately 4 hour intervals i.e., upon arising in morning, midday and late afternoon. Midodrine hydrochloride can cause marked elevation of supine blood pressure. In order to reduce the potential for supine hypertension during sleep, the U.S. FDA has recommended that the last dose should be administered not later than 6 P.M.

After oral administration of an immediate release tablet, the plasma levels of the midodrine peak after about 30 minutes, and decline with a half-life of approximately 25 minutes, while the active metabolite, desglymidodrine, reaches peak blood concentrations about 1 to 2 hours after a dose of midodrine that has been administered and has a half-life of about 3 to 4 hours. The short half-lives of midodrine and desglymidodrine associated with an immediate release tablet requires frequent dosing to maintain desired blood concentration of midodrine and/or desglymidodrine throughout the day.

Patients on immediate release midodrine regimen may experience issues when they take the morning dose since they have to get up and be in upright position. During this phase the blood pressure may fall suddenly as a manifestation of orthostatic hypotension. As such, the current approved dose is limited.

SUMMARY

In the case of midodrine, a pharmaceutically acceptable salt thereof, desglymidodrine, or a pharmaceutically acceptable salt thereof, a major concern is the potential risk of hypertension when administered in a supine position. The immediate release midodrine regimen may require patients to go back in the supine position until the administered dose reaches an effective blood concentration. Patients may have difficulties in pursuing activities throughout the day in an upright position as the level of midodrine decreases with an immediate release regimen with the need to take additional doses as the blood pressure drops. With the possibility of missing an immediate release dose due to high dosing frequency, the patient's condition can become worse and sometimes unmanageable. Overall the multiple dosing of immediate release tablet decreases patient compliance.

It has now been discovered and disclosed herein that if the release of midodrine (or analog thereof) is delayed beyond that of an immediate release formulation and further without having a fast peak plasma concentration of desglymidodrine, the drug may actually be given to a patient in a supine position. As such, the present disclosure provides pharmaceutical compositions of midodrine and/or desglymidodrine or a pharmaceutically acceptable salt thereof. In some embodiments, the composition comprises an effective amount of an active agent selected from midodrine, a pharmaceutically acceptable salt of midodrine, desglymidodrine, a pharmaceutically acceptable salt of desglymidodrine, or a combination thereof wherein the composition is adapted to release midodrine and/or desglymidodrine in such a manner that there is not a fast peak plasma concentration of desglymidodrine. Further, the composition provides a peak plasma concentration which arrives at a time period slower than that of an immediate release formulation. In one embodiment, the peak plasma concentration has a delay of about 30 minutes or greater compared with an immediate release formulation. It is contemplated that the composition can be administered to a human subject in need thereof in a supine position. It is also contemplated that the compositions described herein are administered once a day. In particular, the formulations of midodrine disclosed herein control the plasma levels of the active metabolite of midodrine such that the drug may be given to patients in a supine position. Dose administration in supine position provides a significant advantage to patients, especially those whose orthostatic hypotension is in advanced stage.

In one embodiment, this disclosure provides a pharmaceutical composition comprising an effective amount of an active agent selected from midodrine, a pharmaceutically acceptable salt of midodrine, desglymidodrine, a pharmaceutically acceptable salt of desglymidodrine, or a combination thereof wherein the composition is adapted to release the active agent in such a manner that there is not a fast peak plasma concentration of desglymidodrine.

In another embodiment, this disclosure provides a pharmaceutical composition comprising an effective amount of an active agent selected from midodrine, a pharmaceutically acceptable salt of midodrine, desglymidodrine, a pharmaceutically acceptable salt of desglymidodrine, or a combination thereof; wherein the composition may be administered to a human subject in a supine position.

In some embodiments, this disclosure provides a pharmaceutical composition comprising: (a) a delayed release composition comprising a delayed release agent and (b) an extended release composition comprising (i) an effective amount of an active agent selected from midodrine, a pharmaceutically acceptable salt of midodrine, desglymidodrine, a pharmaceutically acceptable salt of desglymidodrine, or a combination thereof, and (ii) a rate controlling agent; wherein the pharmaceutical composition provides a delayed release period of about 30 min to about 12 hour after administration to a subject and an extended release period after the delayed release period up to about 14 hour after administration to the subject.

In some embodiments, this disclosure provides a pharmaceutical composition comprising: (a) a delayed release composition comprising a delayed release agent and (b) an extended release composition comprising (i) an effective amount of an active agent selected from midodrine, a pharmaceutically acceptable salt of midodrine, desglymidodrine, a pharmaceutically acceptable salt of desglymidodrine, or a combination thereof, and (ii) a rate controlling agent; wherein the pharmaceutical composition provides a delayed release period of about 30 min to about 1 hour after administration to a subject and an extended release period after the delayed release period up to about 14 hour after administration to the subject.

In another embodiment, this disclosure provides a pharmaceutical composition comprising: (a) a delayed release composition comprising a delayed release agent and (b) an extended release composition comprising (i) an effective amount of an active agent selected from midodrine, a pharmaceutically acceptable salt of midodrine, desglymidodrine, a pharmaceutically acceptable salt of desglymidodrine, or a combination thereof, and (ii) a rate controlling agent; wherein the pharmaceutical composition provides a delayed release period of about 8 hours to 12 hours after administration to a subject and an extended release period after the delayed release period up to about 14 hour after administration to the subject.

In some embodiments, the pharmaceutical composition is characterized by an in vitro release profile. For example, the in vitro release profile can be obtained by subjecting the pharmaceutical composition to a USP I (Basket) dissolution test at 100 rpm in 900 mL of 0.1 N HCl at 37° C. In certain embodiments, the in vitro release profile can comprise (a) delayed release of the active agent for a period of about 30 minutes to about 1 hour after start of the dissolution test followed by extended release of the active agent for a period up to about 14 hours, or (b) delayed release of the active agent for up to about 12 hours after start of the dissolution test followed by extended release of the active agent for a period of up to about 14 hours.

In some embodiments, the pharmaceutical composition comprises (a) a delayed release composition comprising a delayed release agent and (b) an extended release composition comprising (i) an effective amount of an active agent selected from midodrine, a pharmaceutically acceptable salt of midodrine, desglymidodrine, a pharmaceutically acceptable salt of desglymidodrine, or a combination thereof, and (ii) a rate controlling agent; wherein the pharmaceutical composition provides a delayed release period of about 30 min to about 12 hour in an in vitro dissolution test with USP I (Basket) at 100 rpm in 900 mL of 0.1 N HCl at 37° C. and an extended release period after the delayed release period up to about 14 hour in the in vitro dissolution test.

In some embodiments, the pharmaceutical composition comprises (a) a delayed release composition comprising a delayed release agent and (b) an extended release composition comprising (i) an effective amount of an active agent selected from midodrine, a pharmaceutically acceptable salt of midodrine, desglymidodrine, a pharmaceutically acceptable salt of desglymidodrine, or a combination thereof, and (ii) a rate controlling agent; wherein the pharmaceutical composition provides a delayed release period of about 30 min to about 1 hour in an in vitro dissolution test with USP I (Basket) at 100 rpm in 900 mL of 0.1 N HCl at 37° C. and an extended release period after the delayed release period up to about 14 hour in the in vitro dissolution test In some embodiments, the pharmaceutical composition comprises (a) a delayed release composition comprising a delayed release agent and (b) an extended release composition comprising (i) an effective amount of an active agent selected from midodrine, a pharmaceutically acceptable salt of midodrine, desglymidodrine, a pharmaceutically acceptable salt of desglymidodrine, or a combination thereof, and (ii) a rate controlling agent; wherein the pharmaceutical composition provides a delayed release period of about 8 hour to about 12 hour in an in vitro dissolution test with USP I (Basket) at 100 rpm in 900 mL of 0.1 N HCl at 37° C. and an extended release period after the delayed release period up to about 14 hour in the in vitro dissolution test.

In some embodiments, the pharmaceutical composition provides an in vitro release profile having no more than a single rise in an extended release rate of the active agent from the extended release composition. In some embodiments, the pharmaceutical composition provides an in vitro release profile without fast initial release. In some embodiments, the pharmaceutical composition provides an in vitro release profile without a second rise.

In some embodiments, less than 10%, less than 9%, less than 8%, less than 7%, less than 6%, less than 5%, less than 4%, less than 3%, less than 2%, or less than 1% by weight of the active agent is released during the delayed release period. In some embodiments, there is no dose dumping from the pharmaceutical compositions disclosed herein over the delayed release period.

In some embodiments, the pharmaceutical composition provides an extended release of the drug throughout the day, e.g., for at least about 10 hours, at least about 11 hours, at least about 12 hours, at least about 13 hours, or at least about 14 hours, when administered to a subject in need thereof. In certain embodiments, the pharmaceutical composition is administered in the morning while the subject is in a supine position. In some embodiments, the pharmaceutical composition is administered in the evening before bed while the subject is in a supine position. In some embodiments, the pharmaceutical composition is administered to a subject in a supine position. In some embodiments, the pharmaceutical composition is administered before the subject's normal sleep at night. In some embodiments, the pharmaceutical composition is administered after the subject's normal waking time in the morning.

In some embodiments, the pharmaceutical composition disclosed herein is formulated for oral administration. In some embodiments, the pharmaceutical composition disclosed herein is administered once daily.

In some embodiments, the pharmaceutical compositions disclosed herein comprises the active agent in an amount between about 2.5 mg and about 150 mg, optionally between about 4 mg to about 50 mg.

In some embodiments, the pharmaceutical compositions disclosed herein provides an in vivo release profile having no fast peak plasma concentration of the active agent.

The present disclosure also provides a method of treating a subject in need thereof, comprising administering to the subject an effective amount of a pharmaceutical composition disclosed herein, wherein the subject has a disorder comprising at least one of: orthostatic hypertension (OH); postural orthostatic tachycardia syndrome (POTS); dysautonomia; symptoms of chronic orthostatic hypotension corresponding to autonomic failure associated with Bradbury-Eggleston syndrome, Shy-Drager syndrome, diabetes mellitus disease, or Parkinson's disease; or retrograde ejaculation. In some embodiments, the subject has a disorder of orthostatic hypertension or postural orthostatic tachycardia syndrome (POTS). In some embodiments, the subject has a disorder of postural orthostatic tachycardia syndrome (POTS). In some embodiments, the subject is 10-25 years old, e.g., 13-18 years old, 13-21 years old, or 13-25 years old. In some embodiments, the subject is male or female. In some embodiments, the subject is male. In some embodiments, the subject is female. In some embodiments, the subject is female, aged 13-25 years old and suffers from POTS. In some embodiments, the subject suffers from Parkinson's disease. In some embodiments, the subject suffers from early-onset Parkinson's disease (e.g., is 50 years old or younger). In some embodiments, the subject is older than 50 years.

In some embodiments, the present disclosure provides a method of reducing the incidence of supine hypertension in a subject in need thereof, comprising administering to the subject an effective amount of a pharmaceutical composition herein.

In some embodiments, the pharmaceutical composition is a tablet or a capsule. In some embodiments, the pharmaceutical composition is an oral suspension and the dosage can be titrated to an effective level for the subject.

DETAILED DESCRIPTION

Definitions

Figure 1:
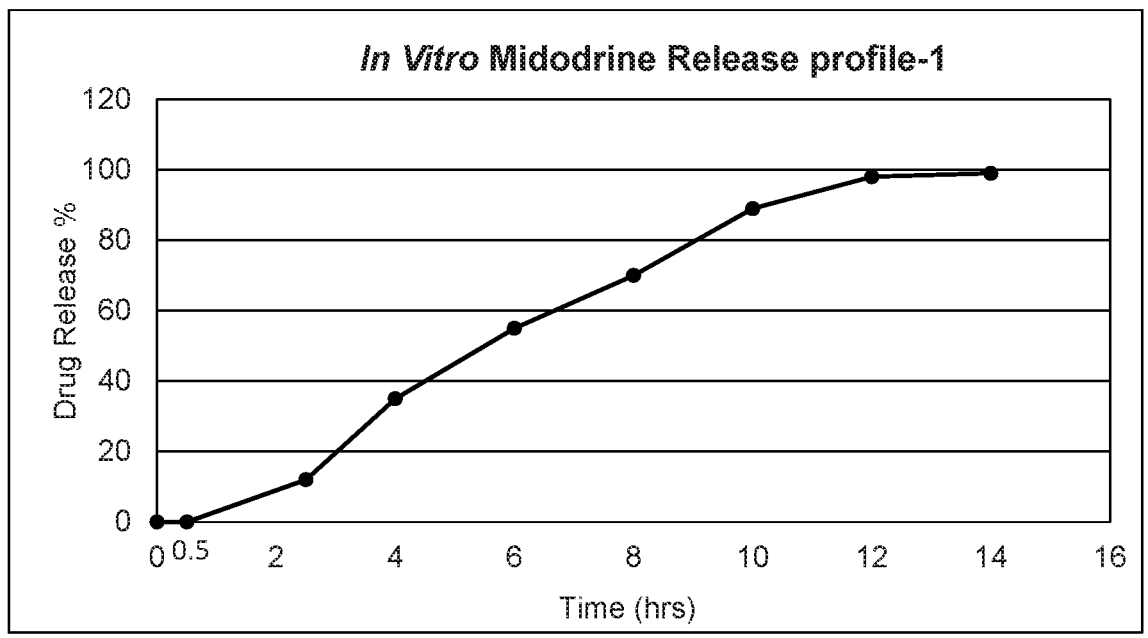
FIG. 1 illustrates in vitro release profile of a midodrine formulation having a lag time for the release of the active agent of about 30 minutes.
Figure 2:
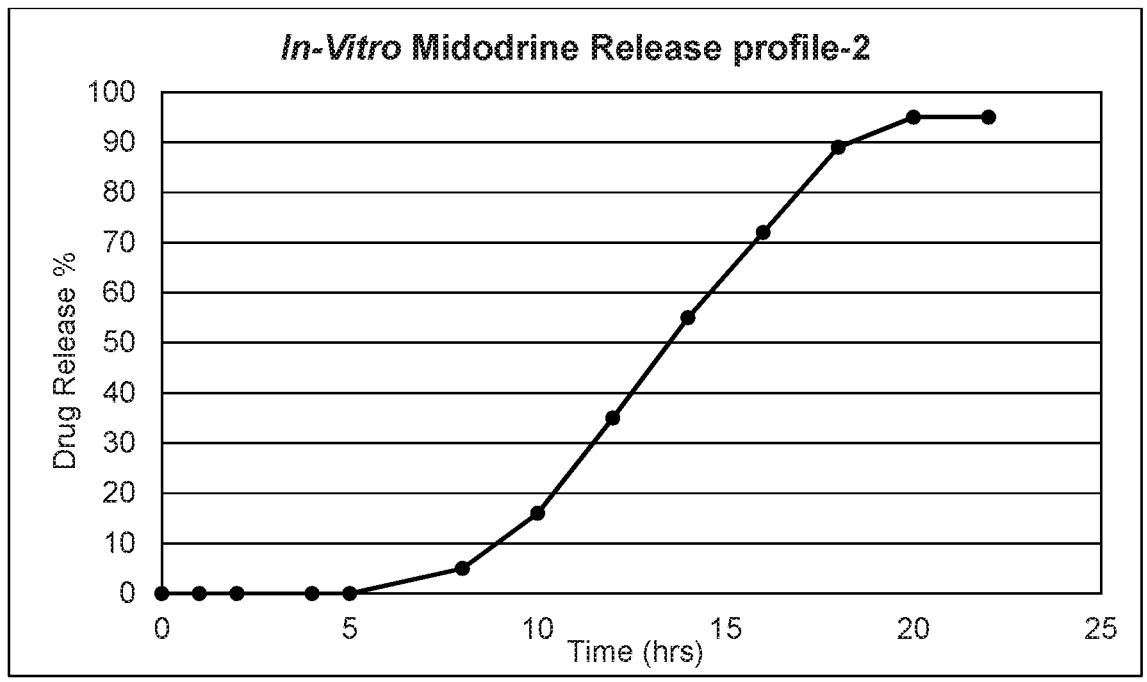
FIG. 2 illustrates in vitro release profile of a midodrine formulation having a lag time for the release of the active agent of about 5 hours.
Figure 3:
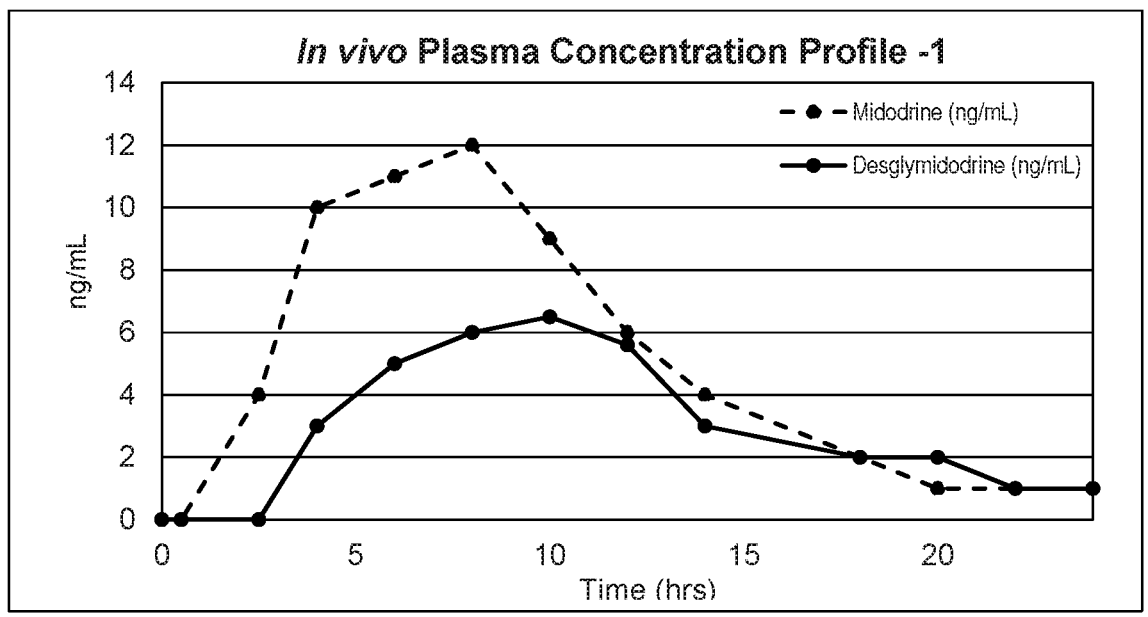
FIG. 3 illustrates in vivo simulated plasma concentration of midodrine and desglymidodrine for the formulation having a lag time for the release of the active agent of about 30 minutes.
Figure 4:
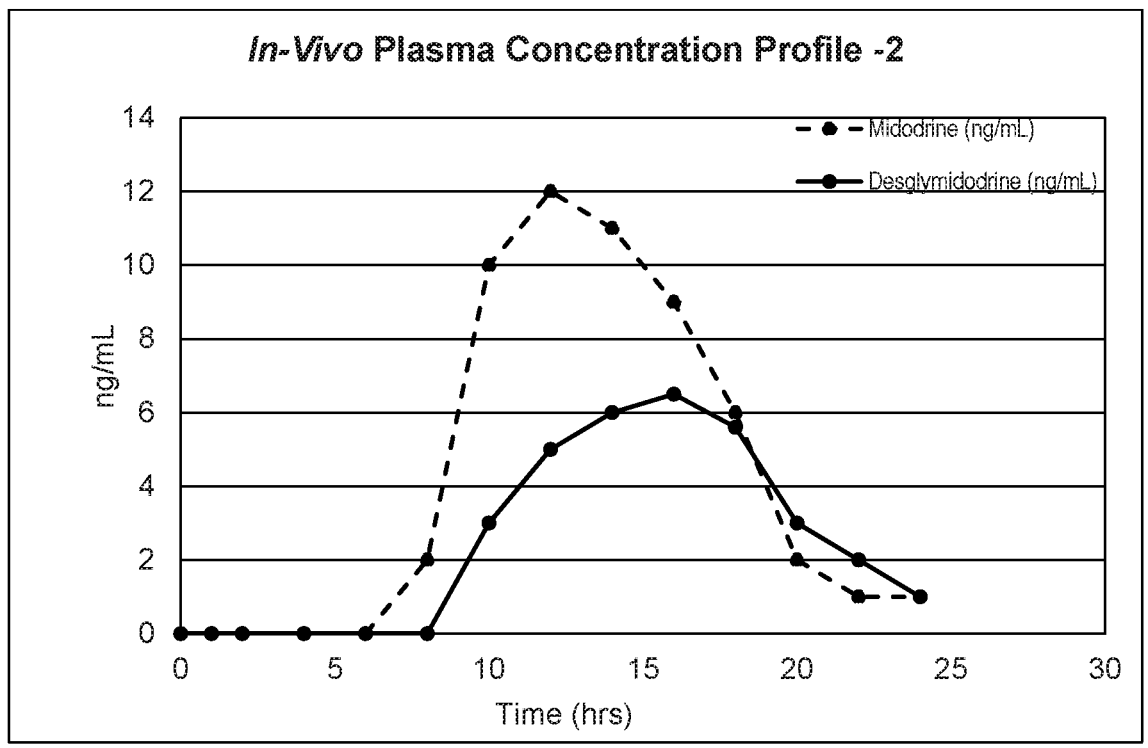
FIG. 4 illustrates in vivo simulated plasma concentration of midodrine and desglymidodrine for the formulation having a lag time for the release of the active agent of about 5 hours.

As used in the present specification, the following words and phrases are generally intended to have the meanings as set forth below, except to the extent that the context in which they are used indicates otherwise.

It is noted that as used in the specification and the appended claims, the singular forms "a," "an," and "the" include plural reference unless the context clearly dictates otherwise.

Also as used herein, "and/or" refers to and encompasses any and all possible combinations of one or more of the associated listed items, as well as the lack of combinations when interpreted in the alternative ("or").

The term "about" refers to a value or parameter that includes (and describes) embodiments that are directed to that value or parameter per se. When the term "about" is used in conjunction with a numerical value or range, it modifies that value or range by extending the boundaries above and below the numerical values set forth. In general, the term "about" is used herein to modify a numerical value above and below the stated value by a variance of 10 percent, up or down (higher or lower), i.e., ±10%, unless a different variance is indicated (e.g., ±30%, ±20%, ±5%, ±1%, etc.). In certain embodiments, the term "about" includes an indicated amount ±10%.

The term "active agent" refers to a substance, including a biologically active substance, that is useful for prophylactic and/or therapeutic treatment. Typically, the active agents are organic molecules that are drug compounds, their salts, metabolites, etc. In some embodiments, the term "active agent" as used in this disclosure refers to midodrine, a pharmaceutically acceptable salt of midodrine, its active metabolite desglymidodrine, a pharmaceutically acceptable salt of desglymidodrine, or a combination thereof. In some embodiments, the active agent is midodrine hydrochloride.

Regarding the active agent, the term "midodrine" refers to the compound having the following chemical structure:

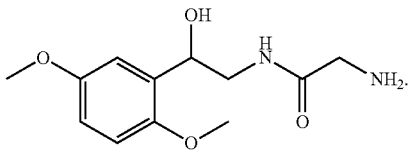 [SMILES: COc1ccc(OC)c(C(O)CNC(=O)CN)c1]

For purposes of this disclosure, unless indicated otherwise, when referring to a formulation or pharmaceutical composition comprising "midodrine", it should be understood that the embodiment can include midodrine or a pharmaceutically acceptable salt of midodrine, e.g., midodrine HCl.

The term "pharmaceutically acceptable salt" of a given compound refers to salts that retain the biological effectiveness and properties of the given compound, and which are not biologically or otherwise undesirable. "Pharmaceutically acceptable salts" include, for example, salts with inorganic acids and salts with an organic acid. In addition, if the compounds described herein are obtained as an acid addition salt, the free base can be obtained by basifying a solution of the acid addition salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from the base compound. Those skilled in the art will recognize various synthetic methodologies that may be used to prepare pharmaceutically acceptable addition salts. Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Likewise, pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines. In one embodiment, a pharmaceutically acceptable salt of midodrine or desglymidodrine is a hydrochloride salt.

The term "desglymidodrine" refers to the active metabolite of midodrine having the following chemical structure:

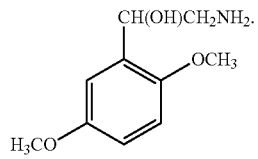

For purposes of this disclosure, unless indicated otherwise, when referring to a formulation or pharmaceutical composition comprising "desglymidodrine", it should be understood that the embodiment can include desglymidodrine or a pharmaceutically acceptable salt of desglymidodrine.

The term "extended release" as used herein refers to a mechanism (delivery system) by which the active agent is released over a specific time period (i.e., an extended release period). In some embodiments, the pharmaceutical composition may extend the release of the active agent over a period up to about 14 hours, from about 4 hours to about 14 hours or more, from about 6 hours to about 12 hours or more, or from about 8 to about 10 hours or more.

"Percent" or "%" as used herein refers to weight (w/w) percentage unless otherwise specified.

The term "percent drug released" as used herein refers to the percentage (w/w) of the active agent released from a pharmaceutical composition at a specified time as compared to the total amount of the active agent in the pharmaceutical composition. For example, if a pharmaceutical composition releases 20 wt % of the total active at 1 hour, 28 wt % at 2 hour, and 35 wt % at 3 hour in a dissolution test, then the percent drug released of this pharmaceutical composition is 20% (w/w) at 1 hour, 28% (w/w) at 2 hour, and 35% (w/w) at 3 hour. "Drug release rate" can be calculated from data of "percent drug released" and has a unit of "percent hour (%/h).

The term "fast peak plasma concentration" as used herein refers to a relatively fast increase of an active agent (e.g., midodrine or desglymidodrine) plasma concentration to a maximum within about 1 hour after administration and a subsequent decrease to below 50% of the maximum within about 2 hours after administration.

The term "initial fast release" as used herein refers to an initial relatively fast release of the active agent from a pharmaceutical composition in an in vitro dissolution test where the composition's dissolution profile includes an increase of the active agent release rate to a maximum within about 1 hour after start of the dissolution test and a subsequent decrease to below 50% of the maximum within about 2 hours after start of the dissolution test.

The term "rise" as used herein refers to an increase of the active agent release rate from a composition to a peak (or shoulder or plateau) in its in vitro dissolution profile. Or, the term "rise" can also refer to an increase of the active agent plasma concentration to a peak (or shoulder or plateau) in its in vivo release profile.

The term "second rise" as used herein refers to an increase of the active agent release rate from a composition after the initial rise. In some embodiments, the second rise is about 5-10 hours after start of an in vitro dissolution test.

The term "lag time" or "delayed release period" refers to a duration of time during which the in vitro release of the active agent of a pharmaceutical composition is delayed or postponed after start of an in vitro dissolutions test, e.g., by use of a barrier coating or a delayed release agent. The term "lag time" or "delayed release period" can also refer to a duration of time during which the in vivo release of the active agent of a pharmaceutical composition is delayed or postponed after administration to a subject, e.g., by use of a barrier coating or a delayed release agent.

The term "barrier coating" or "delayed release coating" refers to a mechanism (delivery system) by which the release of the active agent of a pharmaceutical composition is delayed or postponed for a given period of time (i.e., a delayed release period).

The term "barrier coating agent" or "delayed release agent" refers to an agent that is capable of achieving said lag time or delayed release period for the release of an active agent from a formulation under dissolution conditions designed to mimic in vivo release conditions. The examples of suitable barrier coating agents or delayed release agents include, but are not limited to, acid-insoluble, water-insoluble, water permeable, water impermeable, or water soluble coating polymers such as ethyl cellulose, hydroxypropyl cellulose, hydroxypropyl methylcellulose, sodium carboxymethyl cellulose, cellulose acetate, cellulose acetate butyrate, cellulose acetate phthalate, hydroxypropyl methylcellulose phthalate, hydroxypropyl methylcellulose acetate succinate, alginic acid, methacrylic acid copolymer, copolymer of acrylic acid and methacrylic acid ester, methyl acrylate-methacrylic acid copolymer, polymethylmethacrylate copolymer, polyvinyl acetate/crotonic acid copolymer, polyvinyl alcohol, polyvinyl acetate phthalate, methylmethacrylate copolymer, shellac, polyvinyl acetate, or mixtures thereof, and any other suitable polymers that could be capable of achieving the said lag time in the said dissolution condition. The barrier coating or delayed release coating may further comprise a plasticizer. The non-limiting examples of plasticizers include triacetin, tributyl citrate, triethyl citrate, acetyl tri-n-butyl citrate, diethyl phthalate, castor oil, dibutyl sebacate, acetylated monoglycerides, acetylated diglycerides and the like or mixtures thereof.

The term "rate controlling agent" refers to an agent whose primary function is to modify the duration of release of the active drug substance from the dosage form. The rate controlling agents can be a polymer or a non-polymeric agent. The rate controlling agents can be a hydrophilic polymer or a hydrophobic polymer. The non-limiting examples include hydroxypropyl methyl cellulose (HPMC), hydroxypropyl cellulose (HPC), hydroxyethyl cellulose (HEC) polyethylene oxide, polyvinyl alcohol, polyvinylpyrrolidone, xanthan gum, guar gum, chitosan and its derivatives, carbomer, carrageenan, carboxymethyl cellulose, sodium alginate, polyglycolized glycerides, polyethylenglycol, polyvinyl acetate dispersion, ethyl cellulose, cellulose acetate, cellulose propionate (lower, medium or higher molecular weight), cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), and poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), waxes such as beeswax, carnauba wax, paraffin wax, microcrystalline wax, and ozokerite; fatty alcohols such as cetostearyl alcohol, stearyl alcohol, cetyl alcohol and myristyl alcohol, and fatty acid esters such as glyceryl monostearate; glycerol monooleate, acetylated monoglycerides, tristearin, tripalmitin, cetyl esters wax, glyceryl palmitostearate, glyceryl behenate, and hydrogenated vegetable oils, or a mixture thereof.

The term "treatment" or "treating" means any treatment of a disease in a mammal, including:
  (i) preventing or reducing the incidence of the disease, that is, causing the clinical symptoms of the disease not to develop;
  (ii) inhibiting the disease, that is, arresting the development of clinical symptoms of the disease; and/or
  (iii) relieving the disease, that is, causing the regression of clinical symptoms of the disease.

An "effective amount" is the quantity of compound in which a beneficial clinical outcome may be achieved when the compound is administered to a subject suffering from or at risk of suffering from the described conditions. A "beneficial clinical outcome" may include one or more of: a reduction in number or severity of symptoms in a subject, such as an increase in blood pressure, lack of dizziness and/or lack of light headness. The precise amount of compound administered to a subject may depend on the course of the condition to be treated.

Wherever aspects are described herein with the language "comprising," otherwise analogous aspects described in terms of "consisting of" and/or "consisting essentially of" are also provided. To the extent that the term "includes" or "including" is used in the specification or the claims, it is intended to be inclusive in a manner similar to the term "comprising" as that term is interpreted when employed as a transitional word in a claim.

As used herein, the terms "optional" and "optionally" mean that the subsequently described circumstance may or may not occur, so that the description includes instances where the circumstance occurs and instances where it does not.

Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See Bryan A. Garner, A Dictionary of Modern Legal Usage 624 (2d. Ed. 1995). Also, to the extent that the terms "in" or "into" are used in the specification or the claims, it is intended to additionally mean "on" or "onto." To the extent that the term "substantially" is used in the specification or the claims, it is intended to mean that the identified components have the relation or qualities indicated with degree of error as would be acceptable in the subject industry.

In addition, where features or aspects of the disclosure are described in terms of Markush groups, those skilled in the art will recognize that the disclosure is also thereby described in terms of any individual member or subgroup of members of the Markush group. As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, and the like. As a non-limiting example, each range discussed herein can be readily broken down into a lower third, middle third and upper third, and the like. As will also be understood by one skilled in the art all language such as "up to," "at least," "greater than," "less than," include the number recited and refer to ranges which can be subsequently broken down into sub-ranges as discussed above. Finally, as will be understood by one skilled in the art, a range includes each individual member. For example, a group having 1-3 members refers to groups having 1, 2, or 3 members. Similarly, a group having 1-5 members refers to groups having 1, 2, 3, 4, or 5 members, and so forth. While various aspects and embodiments have been disclosed herein, other aspects and embodiments will be apparent to those skilled in the art.

Pharmaceutical Compositions

The present application provides pharmaceutical compositions, which have improved properties over immediate release and previously disclosed controlled release formulations of midodrine HCl. Currently, there are no marketed controlled release formulations of midodrine.

The pharmaceutical compositions disclosed herein can help improve patient compliance because the pharmaceutical compositions can be administered once daily, either before bedtime or after waking time in the morning and there is no need for a patient to take addition doses during the day. The pharmaceutical compositions disclosed herein also improve patient benefit from midodrine because a patient can take the pharmaceutical compositions while in a supine position. The pharmaceutical compositions disclosed herein provide an extended release of the active agent, and a relatively stable plasma concentration of the active agent, which helps to control the patient's blood pressure in a desired range throughout the day. In some embodiments, if a patient takes the pharmaceutical compositions at night before bedtime, he or she can get up in the morning when the medicine takes effect and can function normally during the day. In some embodiments, if a patient takes the pharmaceutical compositions in the morning after normal waking time, he or she can can take the pharmaceutical compositions in the bed without getting up, e.g., wait to get up when the medicine takes effect (e.g., 30 minutes to an hour), and function normally during the day.

U.S. Pat. No. 6,761,904 refers to a kit comprising a controlled release composition together with one or more relatively fast onset composition for supplemental and individual administration. The '904 states that the controlled release composition was designed to release midodrine and/or desglymidodrine in a relatively fast peak plasma concentration followed by a prolonged and relatively constant plasma concentration of desglymidodrine, and states there is a second rise in release rate that takes place 5-10 hours after start of an in vitro dissolution test.

U.S. Pat. No. 7,070,803 states that compositions that are designed for administration once or twice daily, i.e., a therapeutically effective concentration of desglymidodrine is maintained for a period of at least 10-16 hours followed by a wash out period of about 8-12 hours. The therapeutically effective concentration of desglymidodrine is systemic concentration of desglymidodrine of at least about 3 ng/mL.

The '904 and '803 formulations, however, release midodrine and/or desglymidodrine at a relatively fast first initial rate followed by a slower release rate, then a second rise in the release rate and a decline in the release rate.

Furthermore, there are shortcomings associated with the controlled release formulations and immediate release formulations of midodrine to date since, e.g., they may not be administered to a patient in a supine position due to the potential of hypertension.

In certain aspects, a composition of the present disclosure has a delayed release of the active which reduces the potential risk of hypertension associated with midodrine when administered in a supine position. Thus, the present application provides solutions for improved midodrine formulations with less risk of hypertension and which can be taken in a supine position and a single dose administration of the pharmaceutical composition can deliver midodrine throughout a day.

Certain aspects of the present disclosure are directed to a pharmaceutical compositions comprising an effective amount of an active agent selected from midodrine, a pharmaceutically acceptable salt of midodrine, desglymidodrine, a pharmaceutically acceptable salt of desglymidodrine, or a combination thereof; wherein the composition is adapted to release the active agent in such a manner that there is not a fast peak plasma concentration of desglymidodrine. The present disclosure provides an extended release pharmaceutical composition of midodrine and/or desglymidodrine or a pharmaceutically acceptable salt thereof which can be administered in a supine position. In some embodiments, the composition is administered once a day.

In some embodiments, the present disclosure also provides a barrier or delayed coated pharmaceutical composition of midodrine and/or desglymidodrine or a pharmaceutically acceptable salt thereof.

The pharmaceutical compositions disclosed herein may contain midodrine or a pharmaceutically acceptable salt thereof, wherein midodrine is in a racemic form, in the (R) enantiomeric form or in the (S) enantiomeric form. Similarly, the pharmaceutical compositions disclosed herein may contain desglymidodrine or a pharmaceutically acceptable salt thereof, wherein desglymidodrine is in a racemic form, in the (R) enantiomeric form or in the (S) enantiomeric form.

In one embodiment, this disclosure provides a pharmaceutical composition comprising:
  i. an effective amount of an active agent selected from midodrine, a pharmaceutically acceptable salt of midodrine, desglymidodrine, a pharmaceutically acceptable salt of desglymidodrine, or a combination thereof;
  ii. an effective amount of a barrier coating agent or a delayed release agent to provide for a lag time of the active agent; and
  iii. a rate controlling agent, wherein the composition may be administered to a human subject in a supine position.

As noted above, the release of the active agent is timed such that the drug may be administered to patients in a supine position. In some embodiments, the release time does not allow for a fast peak plasma concentration. In some embodiments, the release time is slower than that of a comparable immediate release formulation. In some embodiments, the barrier coating of the composition provides for this release profile. Further, the composition has an extended release component which may allow for an extended release of the active agent after the lag time. In some embodiments, the release time does not allow for a fast peak plasma concentration, and the extended release rate of the active agent from the pharmaceutical compositions disclosed herein is slower than that of a comparable immediate release formulation.

The present disclosure provides a pharmaceutical composition comprising:
  (a) a delayed release composition comprising a delayed release agent; and
  (b) an extended release composition comprising (i) an effective amount of an active agent selected from midodrine, a pharmaceutically acceptable salt of midodrine, desglymidodrine, a pharmaceutically acceptable salt of desglymidodrine, or a combination thereof, and (ii) a rate controlling agent;
    wherein the pharmaceutical composition provides a delayed release period of about 30 min to about 12 hours after administration to a subject.

In some embodiments, the pharmaceutical composition provides a delayed release period of about 30 min to about 1 hour after administration to a subject. In some embodiments, the pharmaceutical composition provides a delayed release period of about 8 hours to about 12 hour after administration to a subject.

The present disclosure also provides a pharmaceutical composition comprising:
  (a) a delayed release composition comprising a delayed release agent; and
  (b) an extended release composition comprising (i) an effective amount of an active agent selected from midodrine, a pharmaceutically acceptable salt of midodrine, desglymidodrine, a pharmaceutically acceptable salt of desglymidodrine, or a combination thereof, and
(ii) a rate controlling agent;
wherein the pharmaceutical composition provides a delayed release period of about 30 min to about 12 hours in an in vitro dissolution test with USP I (Basket) at 100 rpm in 900 mL of 0.1 N HCl at 37° C.

In some embodiments, the pharmaceutical composition provides a delayed release period of about 30 min to about 1 hour in an in vitro dissolution test. In some embodiments, the pharmaceutical composition provides a delayed release period of about 8 hour to about 12 hour in an in vitro dissolution test.

In some embodiments, in the pharmaceutical compositions disclosed herein, the delayed release composition does not contain midodrine, a pharmaceutically acceptable salt of midodrine, desglymidodrine, or a pharmaceutically acceptable salt thereof. In some embodiments, the active agent is included in the extended release composition only.

Exemplary simulated in vitro dissolution profiles of the compositions disclosed herein are provided in FIGS. 1, 2, 5, 6, 7, 10, and 11. Exemplary simulated target plasma profiles of the compositions disclosed herein are provided in FIGS. 3, 4, 8, and 9. In vitro dissolution testing methods are described herein.

In some embodiments, the in vitro dissolution conditions for delayed release/extended release compositions are designed to mimic the in vivo release conditions.

In a preferred embodiment, the in vitro dissolution test conditions are as follows: 900 mL of 0.1 N HCl in USP apparatus I (basket) at 100 rpm at 37° C. In an alternative embodiment, the dissolution testing conditions can be as follows: 900 mL 0.1 N HCl (pH 1.2) for 0-2 hours; 900 mL acetate buffer (pH 4.5) for 2-4 hours; and 900 mL phosphate buffer (pH 6.8) for 4-14 hours, in USP apparatus I (basket) at 100 rpm at 37° C.

In another embodiment, the release of the active agent from the composition is delayed for a period of one of, or about one of: 15 min, 20 min, 30 min, 45 min, 1 hour, 2 hours, 3 hours, 4 hours, 5 hours, 6 hours, 7 hours, 8 hours, 9 hours, 10 hours, 11 hours, or 12 hours, e.g., about 30 min or 10 hour, or a range between any two of the preceding values, for example, between about 8 hours to 10 hours. In another embodiment, no more than 10% of the active agent, optionally no more than 5%, or no more than 1% is released in the first 30 minutes post administration. The delayed release period, e.g., at least 30 minutes, may be measured by in vitro dissolution conditions known by one skilled in the art. This can be achieved by, but not limited to, applying a barrier coating over drug particles or drug granules or a dosage form which is capable of delaying midodrine release from the formulation in the dissolution condition.

The examples of suitable barrier coating agents (or delayed release agents) include, but are not limited to, acid-insoluble, water-insoluble, water permeable, water impermeable, or water soluble coating polymers such as ethyl cellulose, hydroxypropyl cellulose, hydroxypropyl methylcellulose, sodium carboxymethyl cellulose, cellulose acetate, cellulose acetate butyrate, cellulose acetate phthalate, hydroxypropyl methylcellulose phthalate, hydroxypropyl methylcellulose acetate succinate, alginic acid, methacrylic acid copolymer, copolymer of acrylic acid and methacrylic acid ester, methyl acrylate-methacrylic acid copolymer, polymethylmethacrylate copolymer, polyvinyl acetate/crotonic acid copolymer, polyvinyl alcohol, polyvinyl acetate phthalate, methylmethacrylate copolymer, shellac, polyvinyl acetate, or a mixture thereof, and any other suitable polymers that could be capable of achieving the said lag time in the said dissolution condition.

In one embodiment, this disclosure provides a pharmaceutical composition as described herein, wherein no more than about 10%, about 5%, or about 1% of the active agent may be released in about 30 minutes.

Also as described throughout the composition may be formulated for extended release by incorporating a rate controlling agent. In one embodiment, the composition comprises one or more rate controlling agents. In another embodiment, the one or more rate controlling agents are water-soluble, water-insoluble, water impermeable, and/or water-permeable excipients. The non-limiting examples of rate controlling agents include hydroxypropyl methyl cellulose (HPMC, i.e., hypromellose), hydroxypropyl cellulose (HPC), hydroxyethyl cellulose (HEC) polyethylene oxide, polyvinyl alcohol, polyvinylpyrrolidone (i.e., povidone), xanthan gum, guar gum, chitosan and its derivatives, carbomer, carrageenan, carboxymethyl cellulose, sodium alginate, polyglycolized glycerides, polyethylenglycol, polyvinyl acetate dispersion, ethyl cellulose, cellulose acetate, cellulose propionate (lower, medium or higher molecular weight), cellulose acetate propionate, cellulose acetate butyrate, cellulose acetate phthalate, cellulose triacetate, poly(methyl methacrylate), poly(ethyl methacrylate), poly (butyl methacrylate), poly(isobutyl methacrylate), and poly (hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), waxes such as beeswax, carnauba wax, paraffin wax, microcrystalline wax, and ozokerite; fatty alcohols such as cetostearyl alcohol, stearyl alcohol, cetyl alcohol and myristyl alcohol, and fatty acid esters such as glyceryl monostearate; glycerol monooleate, acetylated monoglycerides, tristearin, tripalmitin, cetyl esters wax, glyceryl palmitostearate, glyceryl behenate, and hydrogenated vegetable oils, or a mixture thereof.

In some embodiments, the rate controlling agent is a hydrophilic polymer selected from hypromellose; hydroxypropyl cellulose (HPC); hydroxyethyl cellulose (HEC); polyethylene oxide; polyvinyl alcohol; povidone; xanthan gum; guar gum; chitosan; a chitosan derivative; carbomer; carrageenan; carboxymethyl cellulose; sodium alginate; a polyglycolized glyceride; polyethylene glycol; a polyvinyl acetate dispersion; cellulose acetate; cellulose acetate butyrate; cellulose acetate phthalate; cellulose triacetate; and a combination thereof.

In some embodiments, the rate controlling agent is a hydrophobic polymer selected from ethyl cellulose; cellulose propionate; cellulose acetate propionate; poly(methyl methacrylate); poly(ethyl methacrylate); poly(methyl acrylate); poly(isopropyl acrylate); poly(isobutyl acrylate); poly (octadecyl acrylate); and a combination thereof.

In some embodiments, the rate controlling agent is a non-polymeric agent selected from a wax; a fatty alcohol; a fatty acid ester; hydrogenated vegetable oil; and a combination thereof.

The pharmaceutical composition may include the extended release composition in a percentage (w/w) of the pharmaceutical composition of one of, or about one of: 5, 10, 15, 20, 25, 30, 35, 40, 45, 50, 55, 60, 65, 70, 75, 80, 85, 90, and 95, e.g., about 40%, or a range between any two of the preceding values, for example, between about 5% (w/w) and about 95% (w/w), between about 30% (w/w) and about 80% (w/w).

In some embodiments, the pharmaceutical composition may include the active agent in an amount in milligrams of one of, or about one of: 2.5, 3, 3.5, 4, 4.5, 5, 5.5, 6, 6.5, 7, 7.5, 8, 8.5, 9, 9.5, 10, 12.5, 15, 17.5, 20, 22.5, 25, 27.5, 30, 32.5, 35, 37.5, 40, 42.5, 45, 47.5, 50, 52.5, 55, 57.5, 60, 62.5, 65, 67.5, 70, 72.5, 75, 77.5, 80, 90, 100, 110, 120, 130, 140, and 150, e.g., about 30 milligrams, or a range between any two of the preceding values, for example, between about 2.5 milligrams and about 150 milligrams or between about 4 milligrams and about 50 milligrams. In some embodiments, the pharmaceutical composition may include the active agent in an amount between 4 milligrams and 50 milligrams.

The pharmaceutical compositions disclosed herein may further comprise pharmaceutically acceptable excipients which are ingredients that do not substantially have any therapeutic or prophylactic effect per se. The non-limiting examples of pharmaceutically acceptable excipients include diluents, binders, fillers, disintegrants, glidants, lubricants, surfactants, etc. Other pharmaceutically acceptable excipients include colorants, flavoring agents, solubilizing agents, buffering agents, pH adjusting agents and wetting agents, plasticizers, sweeteners, thickeners, film formers, stabilizers, permeation enhancers, saliva stimulating agents, etc.

In some embodiments, the pharmaceutical composition can comprise a delayed release composition comprising at least one of: a delayed release agent, a delayed release coating; a mucoadhesive; a film-forming, soluble polymer; a disintegrant; a soluble binder; a fluid carrier; a gastric fluid-swellable composition; multiparticles, and a gastric fluid gas generating agent.

1. Pharmaceutical Compositions with a Delayed Release Coating

In some embodiments, the pharmaceutical compositions disclosed herein comprise one or more delayed release coatings.

In some embodiments, the pharmaceutical compositions comprise an extended release core and a delayed release coating. In some embodiments, the delayed release coating is present in a percentage (w/w) of the pharmaceutical composition of one of, or about one of: 3, 4, 5, 6, 7, 8, 9, 10, 11, 12, 13, 14, 15, 16, 17, 18, 19, 20, 22, 24, 26, 28, 30, 35, 40, 45, 50, 55, 60, 65, 70, 75, 80, 85, and 90, e.g., about 5%, about 10%, about 15%, or about 20%, or a range between any two of the preceding values, for example, between about 3% (w/w) and about 50% (w/w), between about 5% (w/w) and about 25% (w/w), between about 5% (w/w) and about 20% (w/w), between about 5% (w/w) and about 10% (w/w), or between about 10% (w/w) and about 20% (w/w). In some embodiments, the delayed release coating comprises OPADRY (hypromellose-containing premix), SURELEASE (ethylcellulose-containing premix).

In some embodiments, no more than 0.1%, 0.5%, 1%, 2%, 3%, 4%, 5%, 6%, 7%, 8%, 9% or 10% (w/w) of the active agent is released within the delayed release period, e.g., within 30 min, within 45 min, within 1 hour, within 8 hours, within 10 hours, or within 12 hours. In some embodiments, there is no dose dumping from the pharmaceutical compositions disclosed herein over the delayed release period. In some embodiments, no more than 10%, no more than 5%, or no more than 1% of the active agent is released from the pharmaceutical composition disclosed herein in a dose dumping test. The following dissolution conditions are used to test for dose dumping.

Testing Conditions for Dose Dumping of formulation are as follows: 900 mL, 0.1 N HCl, USP basket (USP I), 100 rpm, with or without alcohol.

Test 1: 12 units tested according to the proposed method with 0.1N HCl, with data collected every 15 minutes for a total of 2 hours;

Test 2: 12 units analyzed by substituting 5% (v/v) of test medium with Alcohol USP and data collection every 15 minutes for a total of 2 hours;

Test 3: 12 units analyzed by substituting 20% (v/v) of test medium with Alcohol USP and data collection every 15 minutes for a total of 2 hours;

Test 4: 12 units analyzed by substituting 40% (v/v) of test medium with Alcohol USP and data collection every 15 minutes for a total of 2 hours.

In some embodiments, the pharmaceutical composition may be configured as a compressed tablet for delayed release/extended release (DR/ER). The pharmaceutical composition may include a core. The core may include the active agent in an amount between about 2.5 milligrams and about 150 milligrams or between about 4 milligrams and about 50 milligrams. The core may include a rate controlling agent in a percentage (w/w) of the pharmaceutical composition of between about 65% (w/w) and about 95% (w/w). The pharmaceutical composition may include, surrounding the core, a delayed release coating in a percentage (w/w) of the pharmaceutical composition of between about 3% (w/w) and about 50% (w/w). The extended release composition may include one or more of: microcrystalline cellulose, hypromellose, and povidone. The delayed release coating may include one or more of: hypromellose and ethyl cellulose.

2. Pharmaceutical Compositions Comprising a Mucoadhesive Agent

In some embodiments, the pharmaceutical compositions disclosed herein comprise a delayed release composition comprising a mucoadhesive agent.

In some embodiments, the mucoadhesive agent may include one or more of: a carbomer, methyl cellulose, sodium carboxymethyl cellulose, hydroxyl ethyl cellulose, hydroxyl propyl cellulose, hypromellose, a polyalkylene glycol, a polyamide, a polyglycolide, a polylactide-co-glycolide, esters of hyaluronic acid, gelatin, polyacrylic acid, polyacrylic acid co-acrylamide, polyalkyl cyanoacrylate, polycaprolactone, polycarbophil, polyethyleneoxide, polylactide, polymethacrylic acid, polymethylmethacrylic acid, polyvinyl acetate, polyvinyl alcohol, polyvinyl pyrrolidone, poly(methylacrylate acid) cysteine, poly vinyl pyrollidone-vinyl acetate, a plant gum, karaya gum, lectin, carrageenan, sodium alginate, tragacanth, xanthan gum, guar gum, and modified guar gum.

In some embodiments, the mucoadhesive agent can be present in a delayed release coating. In some embodiment, the mucoadhesive agent can be present in an additional layer on top of the delayed release coating. In some embodiments, the delayed release composition can include EUDRAGIT L30 D-55 (a poly(meth)acrylate polymer), hypromellose, silicified microcrystalline cellulose, and sodium carboxymethyl cellulose.

In some embodiments, the pharmaceutical composition may include a mucoadhesive agent in a percentage (w/w) of the pharmaceutical composition of one of, or about one of: 5, 10, 15, 20, 25, 30, 35, 40, 45, 50, 55, 60, 65, and 70, e.g., about 40%, or a range between any two of the preceding values, for example, between about 5% (w/w) and about 70% (w/w).

3. Pharmaceutical Compositions Comprising a Gastric Swellable Composition

In several embodiments, the pharmaceutical composition may be configured as a delayed release/extended release compressed tablet for gastric retention by size. The pharmaceutical composition may include the active agent in an amount between about 2.5 milligrams and about 150 milligrams or between about 4 milligrams and about 50 milligrams. The pharmaceutical composition may include an extended release composition in a percentage (w/w) of the pharmaceutical composition of between about 15% (w/w) and about 65% (w/w). The pharmaceutical composition may include a delayed release coating in a percentage (w/w) of the pharmaceutical composition of between about 3% (w/w) and about 50% (w/w). The pharmaceutical composition may further include a gastric swellable (also referred to as "gastric fluid-swellable") composition in a percentage (w/w) of the pharmaceutical composition of between about 40% (w/w) and about 80% (w/w). The extended release composition may include one or more of: microcrystalline cellulose, hypromellose, and ethyl cellulose. The delayed release coating may include an anionic copolymer based on methyl acrylate, methyl methacrylate and methacrylic acid. The gastric swellable composition may include one or more of: hypromellose, hydroxypropyl cellulose and xanthan gum.

In some embodiments, the gastric swellable composition comprises hypromellose, swellable starch, or a combination thereof.

In some embodiments, the gastric swellable composition can be present in a delayed release coating. In some embodiments, the gastric swellable composition can be present outside a delayed release coating. In some embodiments, the delayed release composition can include EUDRAGIT L30 D-55 (a poly(meth)acrylate polymer), hypromellose, silicified microcrystalline cellulose, and polyethylene oxide.

In some embodiments, the gastric swellable composition is present in a percentage (w/w) of the pharmaceutical composition of one of, or about one of: 5, 10, 15, 20, 25, 30, 35, 40, 45, 50, 55, 60, 65, and 70, e.g., about 40%, or a range between any two of the preceding values, for example, between about 5% (w/w) and about 70% (w/w).

4. Pharmaceutical Compositions Comprising a Gastric Gas-Generating Composition

In various embodiments, the pharmaceutical composition may be configured as a delayed release/extended release compressed tablet suitable for gastric retention by buoyancy. The pharmaceutical composition may include the active agent in an amount between about 2.5 milligrams and about 150 milligrams or between about 4 milligrams and about 50 milligrams. The pharmaceutical composition may include a gastric swellable composition in a percentage (w/w) of the pharmaceutical composition of between about 40% (w/w) and about 80% (w/w). The pharmaceutical composition may further include a gastric gas-generating (also referred to as "gastric fluid gas-generating") composition in a percentage (w/w) of the pharmaceutical composition of between about 5% (w/w) and about 20% (w/w). The extended release composition may include one or more of: microcrystalline cellulose, hypromellose, and ethyl cellulose. The delayed release coating may include an anionic copolymer based on methyl acrylate, methyl methacrylate and methacrylic acid. The gastric swellable composition may include one or more of: hypromellose, hydroxypropyl cellulose and xanthan gum. The gastric gas-generating composition may include sodium bicarbonate.

In some embodiments, the gastric gas-generating composition may include one or more of an alkali metal bicarbonate and an alkali metal carbonate, e.g., carbonate or bicarbonate salts of lithium, sodium, potassium, magnesium, and calcium, such as sodium bicarbonate.

In some embodiments, the gastric gas-generating composition can be present in a delayed release coating. In some embodiments, the gastric gas-generating composition can be present outside a delayed release coating. In some embodiments, the delayed release composition can include EUDRAGIT L30 D-55 (a poly(meth)acrylate polymer), hypromellose, silicified microcrystalline cellulose, and sodium, bicarbonate.

In some embodiments, the pharmaceutical composition disclosed herein can include a gastric gas-generating composition in a percentage (w/w) of the pharmaceutical composition of one of, or about one of: 1, 2, 3, 4, 5, 6, 7, 8, 9, 10, 12, 14, 16, 18, 20, 22, 24, 26, 28, 30, 35, 40, 45, and 50 e.g., about 10%, or a range between any two of the preceding values, for example, between about 1% (w/w) and about 50% (w/w).

In some embodiments, the present disclosure also provides pharmaceutical compositions comprising a combination of gastric retention methods disclosed herein. For example, a delayed release composition can include a delayed release coating, a mucoadhesive agent, a gastric swellable composition, and/or a gastric gas-generating composition. In another embodiment, a delayed release composition can include a mucoadhesive agent, a gastricswellabe agent, a gastric gas generating agent and a combination thereof 5. Pharmaceutical Compositions Comprising Multi-Particulates In some embodiments, the pharmaceutical compositions disclosed herein comprise a plurality of particulates. Each particulate may include a particulate core (i.e., the extended release composition) that may include the active agent and a rate controlling agent. Each particulate may include a particulate coating that includes a delayed release coating. The plurality of particulates may be characterized by the active agent in an amount between about 2.5 milligrams and about 150 milligrams or between about 4 milligrams and about 50 milligrams. The plurality of particulates may be characterized by the extended release composition in a percentage (w/w) of the pharmaceutical composition of between about 55% (w/w) and about 95% (w/w). The plurality of particulates may be characterized by the delayed release coating in a percentage (w/w) of the pharmaceutical composition of between about 5% (w/w) and about 20% (w/w). The extended release composition may include one or more of: hypromellose, ethyl cellulose, and microcrystalline cellulose. The delayed release coating may include ethyl cellulose.

In some embodiments, the pharmaceutical composition may be formed as a lipid matrix multi-particulate. The pharmaceutical composition may include a plurality of particulates. Each particulate may include a particulate core (i.e., the extended release composition) that may include the active agent and a rate controlling agent. Each particulate core may include the extended release composition including a matrix incorporating the active agent. The core, e.g., the matrix, may further include a lipid. The extended release composition may further include a sub-coat surrounding the core. The delayed release coating may surround the particulate core. The pharmaceutical composition may be characterized by the active agent in an amount between about 2.5 milligrams and about 150 milligrams or between about 4 milligrams and about 50 milligrams. The pharmaceutical composition may include the extended release composition in a percentage (w/w) of the pharmaceutical composition of between about 45% (w/w) and about 85% (w/w). The pharmaceutical composition may include the delayed release coating in a percentage (w/w) of the pharmaceutical composition of between about 5% (w/w) and about 20% (w/w). The extended release composition may include one or more of: glycerol dibehenate, a poloxamer, and microcrystalline cellulose. In some embodiments, the poloxamer is poloxamer 407. In some embodiments, the pharmaceutical composition can include a sub-coat comprising hypromellose. The delayed release coating may include one or more of: hypromellose pthlalate and triethyl citrate.

In several embodiments, the pharmaceutical composition may be formed as a hydrophilic matrix multi-particulate. The pharmaceutical composition may include a plurality of particulates. Each particulate may include a particulate core (i.e., the extended release composition) that may include the active agent and a rate controlling agent. Each particulate may include the delayed release coating. The pharmaceutical composition may include the active agent in an amount between about 2.5 milligrams and about 150 milligrams or between about 4 milligrams and about 50 milligrams. The pharmaceutical composition may include the extended release composition in a percentage (w/w) of the pharmaceutical composition of between about 50% (w/w) and about 95% (w/w). The pharmaceutical composition may include the delayed release coating in a percentage (w/w) of the pharmaceutical composition of between about 5% (w/w) and about 20% (w/w). The extended release composition may include one or more of: hypromellose, povidone, and microcrystalline cellulose. The delayed release coating may include one or more of: hypromellose phthalate and triethyl citrate.

In various embodiments, the pharmaceutical composition may be formed as a drug-coated multi-particulate. The pharmaceutical composition may include a plurality of particulates. Each particulate may include a particulate core. Each particulate core (i.e., the extended release composition) may include a pharmaceutically inert core, the active agent, and a rate controlling agent. Each particulate may include a particulate coating that includes the delayed release coating. The plurality of particulates may be characterized by the active agent in an amount between about 2.5 milligrams and about 150 milligrams or between about 4 milligrams and about 50 milligrams. The plurality of particulates may be characterized by the pharmaceutically inert core in a percentage (w/w) of the pharmaceutical composition of between about 65% (w/w) and about 85% (w/w). The plurality of particulates may be characterized by the delayed release coating in a percentage (w/w) of the plurality of particulates of between about 5% (w/w) and about 20% (w/w). The pharmaceutically inert core may include sugar microspheres or microcrystalline cellulose microspheres. The extended release composition may include one or more of: hypromellose and ethyl cellulose. The delayed release coating may include ethyl cellulose.

In some embodiments, the pharmaceutical composition may be configured in the form of an orally disintegrating tablet. The pharmaceutical composition may include a plurality of particulates compressed together with the disintegrating composition to form the compressed orally disintegrating tablet. The particulate is described herein and may include a particulate coating that includes a delayed release coating. The plurality of particulates may be characterized by the active agent in an amount between about 2.5 milligrams and about 150 milligrams or between about 4 milligrams and about 50 milligrams. The pharmaceutically acceptable inert core may include sugar microspheres. The extended release composition may include one or more of: hypromellose and ethyl cellulose. The delayed release coating may include ethyl cellulose. The disintegrating composition may include one or more of: crospovidone, sodium starch glycolate, and croscarmellose sodium.

In some embodiments, the pharmaceutical composition may be configured in the form of a liquid suspension, for example, comprising a plurality of particulates disclosed herein and a suspending vehicle. The suspending vehicle may include one or more of: water, ethanol, a vegetable oil, a suspending agent (such as xanthan gum), a surfactant, a preservative, a pH modifier, a sweeteners, a coloring agent, and a flavoring agent. The pharmaceutical composition may include the suspending vehicle in a percentage (w/w) of the pharmaceutical composition of one of, or about one of: 30, 35, 40, 45, 50, 55, 60, 65, 70, 75, 80, 85, 90, and 95, e.g., about 60%, or a range between any two of the preceding values, for example, between about 30% (w/w) and about 95% (w/w).

In some embodiments, the pharmaceutical composition can further comprise an immediate release composition comprising an effective amount of the active agent, wherein the immediate release composition releases the active agent after the delayed release period. The amount of the active agent in the immediate release composition can be in a percentage (w/w) of the total active agent in the pharmaceutical composition of one of, or about one of: 5%, 10%, 20%, 30%, 40%, and 50%, e.g., about 30%, or a range between any two of the preceding values, for example, between about 20% (w/w) and about 40% (w/w). In one embodiment, the pharmaceutical composition can be bilayer tablets, containing (1) granules having an immediate release drug layer and a delayed release layer, and (2) granules having an extended release composition and a delayed release layer. In another embodiment, the pharmaceutical composition can be multiparticulates.

In some embodiments, the pharmaceutical composition can comprise one or more pulsatile drug delivery systems. Pulsatile drug delivery systems are known in the art. Pulsatile release can be realized by incorporating different kinds (e.g., three kinds) of extended release pellets that each starts releasing the drug at a different time. For example, the first type pellets ($1^{st}$ pulse) coated with a 30 min delay coating release the drug for a period of 4 hours. (The 30 min delay is to enable the subject taking the medication in a supine position.) The $2^{nd}$ type coated pellets ($2^{nd}$ pulse) will not release any drug until 4 hours later and extend the drug release for another 4 hours. The $3^{rd}$ type coated pellets ($3^{rd}$ pulse), similarly to the $2^{nd}$ type pellets, will not release the drug until 8 hours later and extend for 4 hours, thus for a total of 12 hours extended release.

Pulsatile release pellets for each pulse have a delayed release composition that controls their delayed release periods. In some embodiments, the first type pellets have a delayed release period about 30 min to about 1 hour, the second type pellets have a delayed release period about 3 hour to about 5 hour, and the third type pellets have a delayed release period about 6 hour to about 10 hour.

Pulsatile release pellets for each pulse can release the same or different amounts of the active agent. In some embodiments, pulsatile release pellets for each pulse releases the same amount of the active agent. In some embodiments, pulsatile release pellets for each pulse releases a different amount of the active agent.

Pulsatile release pellets for each pulse can have the same or different extended release periods. In some embodiments, pulsatile release pellets for each pulse have the same extended release period, such as about 4 hours. In some embodiments, pulsatile release pellets for each pulse have a different extended release period.

In another embodiment, the pharmaceutical compositions disclosed herein can be administered with or without water.

In one embodiment, the pharmaceutical compositions disclosed herein are formulated for oral administration. The composition is in the form of an orally disintegrating tablet, a mouth dissolving tablet, a chewable tableta buccal adhesive tablet, a buccal adhesive film, a sublingual tablet, an oral suspension, or a powder for oral suspension, or a granule for oral suspension, a tablet for oral suspension, a gastroretentive drug delivery system, or a combination thereof. Suitable formulations are known in the art or are described herein. In some embodiments, the pharmaceutical compositions disclosed herein are in the form of an oral suspension.

In some embodiments, the pharmaceutical composition is in the form of an extended release tablet, a multiparticulate drug delivery, an oral suspension, a powder for oral suspension, a granule for oral suspension, a tablet for oral suspension, a gastroretentive drug delivery system, or a combination thereof.

In various embodiments, the pharmaceutical composition may include one or more of: a diluent, a binder, a filler, a disintegrant, a glidant, a lubricant, a surfactant, a colorant, a flavoring agent, a solubilizing agent, a buffering agent, a pH adjusting agent, a wetting agent, a plasticizer, a sweetener, a thickener, a film former, a stabilizer, a saliva stimulating agent, a preservative, an alcohol, a vegetable oil, and water. For example, the pharmaceutical composition may include a plasticizer. The plasticizer may include one or more of: triacetin, tributyl citrate, triethyl citrate, acetyl tri-n-butyl citrate, diethyl phthalate, castor oil, dibutyl sebacate, an acetylated monoglyceride, and an acetylated diglyceride.

In several embodiments, the pharmaceutical composition may include a disintegrant. The disintegrant may include one or more of: crospovidone, croscarmellose sodium, sodium starch glycolate, and pregelatinized starch. The pharmaceutical composition may include the disintegrant in a percentage (w/w) of the pharmaceutical composition of one of, or about one of: 1, 5, 10, 15, and 20, e.g., about 10%, or a range between any two of the preceding values, for example, between about 1% (w/w) and about 20% (w/w).

In various embodiments, the pharmaceutical composition may include a binder.

The binder may include one or more of: sucrose, lactose, xylitol, sorbitol, maltitol, mannitol, microcrystalline cellulose, gelatin, povdone, polyethylene glycol, starch, hydroxyethyl cellulose, hydroxypropyl cellulose, hydroxyethyl methyl cellulose, hypromellose, and ethyl hydroxyethyl cellulose. The pharmaceutical composition may include the binder in a percentage (w/w) of the pharmaceutical composition of one of, or about one of: 1, 5, 10, 15, and 20, e.g., about 10%, or a range between any two of the preceding values, for example, between about 1% (w/w) and about 20% (w/w).

In some embodiments, the pharmaceutical composition may include a film-forming polymer. The film-forming polymer may include one or more of: sodium alginate, pullulan, pectin, gelatin, polyvinyl alcohol, hydroxy propyl cellulose, hypromellose, sodium carboxy methyl cellulose, ethyl cellulose, povidone, polyethylene oxide, and a polyacrylate. The pharmaceutical composition may include the film-forming polymer in a percentage (w/w) of the pharmaceutical composition of one of, or about one of: 5, 10, 15, 20, 25, 30, 35, 40, 45, 50, 55, 60, 65, and 70, e.g., about 40%, or a range between any two of the preceding values, for example, between about 5% (w/w) and about 70% (w/w).

In Vitro and In Vivo Release Profile

In several embodiments, the pharmaceutical composition may be characterized by an in vitro release profile. The in vitro release profile may be obtained by subjecting the pharmaceutical composition to a USP I (Basket) dissolution test at 100 rpm in 900 mL of 0.1 N HCl at 37° C. As examples of in vitro release profiles, see, for example, a delayed release of the active agent for a period of about 30 minutes, or up to about 10 hours or 12 hours followed by, for example, an extended release of the active agent for a period of about 10 hours or 12 hours.

In some embodiments, the pharmaceutical composition provides an in vitro release profile having no more than a single rise in an extended release rate of the active agent from the extended release composition. In some embodiments, the pharmaceutical composition provides an in vitro release profile without fast initial release. In some embodiments, the pharmaceutical composition provides an in vitro release profile without a second rise.

In some embodiments, the pharmaceutical compositions disclosed herein provides an in vivo release profile having no fast peak plasma concentration of the active agent.

In some embodiments, the pharmaceutical composition disclosed herein may be effective such that the in vivo release profile contains no more than a single rise in the peak plasma concentration of the active agent. In some embodiments, the pharmaceutical composition disclosed herein has an in vivo release profile having a single rise in the peak plasma concentration of the active agent. In other words, the pharmaceutical composition has an in vivo release profile that does not have a second rise in the peak plasma concentration of the active agent.

The pharmaceutical composition may be effective such that the release profile may be characterized by the single rise in an extended release rate of the active agent over an extended release period, the single rise in the extended release rate occurring at a beginning of the extended release period. It is important that the pharmaceutical compositions disclosed herein have uniformity in dose units. In some embodiments, the dosage units of the pharmaceutical compositions disclosed herein may be characterized by that the drug release rate of the dosage units at a given time has a percent standard deviation of less than-about one of ±1, 2, 3, 4, 5, 6, 7, 8, 9, 10, 11, 12, 13, 14, 15, 16, 17, 18, 19, and 20, e.g., within a percentage range of about ±10%.

The extended release composition may be effective such that the release profile includes an extended release of greater than about 70% (w/w) of the active agent in the pharmaceutical composition over an extended release period in hours of at least one of, or at least about one of: 4, 5, 6, 7, 8, 9, 10, 11, 12, 13, and 14, e.g., about 10 hours, or a range between any two of the preceding values, for example, of between about 4 hours and about 14 hours. The extended release composition may be effective such that the release profile is characterized by an extended release period starting from an initial rise in release of the active agent to a time corresponding to release of about 70% of the active agent from the extended release composition. The extended release period may be a time in hours of at least one of, or at least about one of: 4, 4.5, 5, 5.5, 6, 7, 8, 9, 10, 11, 12, 13, and 14, e.g., at least about 4 hours, or a range between any two of the preceding values, for example, between about 4 hours and about 14 hours.

The delayed release coating may be effective such that the in vitro release profile is characterized by a delayed release period from the beginning of the dissolution test in hours of at least one of, or at least about one of: 0.25, 0.5, 1, 1.5, 2, 2.5, 3, 3.5, 4, 4.5, 5, 6, 7, 8, 9, 10, 11, 12, 13, and 14, e.g., at least about 0.5 hours, or a range between any two of the preceding values, for example, between about 0.25 hours and about 10 hours. The delayed release period may be characterized by an amount of the active agent released, in percentage (w/w), of less than one of, or less than about one of: 10%, 5%, 4%, 3%, 2%, 1.5%, 1%, 0.75%, 0.5%, 0.25%, and 0.1%, e.g., less than about 4%. The delayed release period may be characterized by a rate of release of the active agent, in percentage (w/w) per hour, of less than one of, or less than about one of: 5%, 4%, 3%, 2%, 1.5%, 1%, 0.75%, 0.5%, 0.25%, and 0.1%, e.g., less than about 4% per hour. The delayed release coating may be effective such that the release profile is characterized by a delayed release period from the beginning of the dissolution test in hours of at least one of, or at least about one of: 0.25, 0.5, 1, 1.5, 2, 2.5, 3, 3.5, 4, 4.5, 5, 6, 7, 8, 9, 10, 11, 12, 13, and 14, e.g., at least about 0.5 hours, or a range between any two of the preceding values, for example, between 8 hours and 10 hours, or between 10 hours and 12 hours.

The extended release composition may effective such that the release profile is characterized by an extended release period in hours of at least one of, or at least about one of: 4, 4.5, 5, 5.5, 6, 7, 8, 9, 10, 11, 12, 13, and 14, e.g., at least about 4 hours, or a range between any two of the preceding values, for example, of between about 4 hours and about 14 hours.

In some embodiments, the delayed release composition may be effective such that the delayed release period is between 0.5 hours and 10 hours. The extended release composition may be effective such that the extended release period is between 4 hours and 14 hours. The extended release composition may be effective to extend the release of the active agent over an extended release period. The release profile may be characterized at a time from the start of the extended release period, by a percent (w/w) of the total amount of active agent in the pharmaceutical composition, of: a drug release rate of 1% to 15% per hour.

In several embodiments, administration of the pharmaceutical composition to a subject may result in a maximum plasma concentration ($C_{max}$) of the active metabolite in the subject in the range of about 2 ng/mL to about 100 ng/mL after oral administration. Administration of the pharmaceutical composition may result in the plasma level of the active metabolite, desglymidodrine, in a subject of at least 3 ng/mL for a duration of at least about 4 hours, at least about 6 hours, at least about 8 hours, at least about 12 hours, and at least about 14 hours.

Methods of Treatment

The present disclosure provides methods of using the pharmaceutical compositions of midodrine and/or desglymidodrine or a pharmaceutically acceptable salt thereof, as described herein. In one embodiment is provided a method of treating orthostatic hypotension in a human subject in need thereof comprising administering to the subject a composition as described herein. In one embodiment, the composition is administered to the subject in a supine position. In one embodiment, the composition is administered once a day. In some embodiments, the pharmaceutical composition maintains blood pressure of the subject within desired levels (e.g., 80 to 120 mmHg) throughout the day.

The pharmaceutical compositions disclosed herein are useful for the treatment of orthostatic hypotension, but are not limited to orthostatic hypotension and can be used to treat other conditions like dysautonomia.

The pharmaceutical compositions of the present disclosure can also be used to treat or reduce the incidence of a disorder including at least one of: orthostatic hypotension; postural orthostatic tachycardia syndrome (POTS); dysautonomia; symptoms of chronic orthostatic hypotension corresponding to autonomic failure associated with Bradbury-Eggleston syndrome, Shy-Drager syndrome, diabetes mellitus disease, and Parkinson's disease; and retrograde ejaculation. In some embodiments, the pharmaceutical compositions of the present disclosure can be used to reduce the incidence of supine hypertension in a subject in need thereof. In some embodiments, the pharmaceutical compositions of the present disclosure can be used to treat a subject suffering from Parkinson's disease. In some embodiments, the pharmaceutical compositions of the present disclosure can be used to treat a subject suffering from or at risk of suffering from postural orthostatic tachycardia syndrome (POTS).

In certain aspects, the method is directed to treating a subject suffering from or at risk of suffering from orthostatic hypotension due to autonomic failure comprising administering an effective amount of the pharmaceutical composition disclosed herein to a subject in need thereof. In some embodiments, the subject suffers from Bradbury-Eggleston, Shy-Drager syndromes, diabetes mellitus disease, or Parkinson's disease.

In certain aspects, the method is directed to treating a subject having Parkinson's disease who suffers from or is at risk of suffering from orthostatic hypotension comprising administering an effective amount of a pharmaceutical composition disclosed herein to a subject in need thereof.

In certain aspects, the method is directed to treating a subject having postural orthostatic tachycardia syndrome (POTS) who suffers from or is at risk of suffering from orthostatic hypotension comprising administering an effective amount of a pharmaceutical composition disclosed herein to a subject in need thereof.

In some embodiments, the subject is 10-25 years old, e.g., 13-18 years old, 13-21 years old, or 13-25 years old. In some embodiments, the subject is male or female. In some embodiments, the subject is male. In some embodiments, the subject is female. In some embodiments, the subject is female, aged 13-25 years old and suffers from POTS. In some embodiments, the subject suffers from Parkinson's disease. In some embodiments, the subject suffers from early-onset Parkinson's disease (e.g., is 50 years old or younger). In some embodiments, the subject is older than 50 years.

In certain embodiments, the method is directed to treating or reducing the incidence of supine hypertension in a subject in need thereof, comprising administering to the subject a an effective amount of the pharmaceutical composition disclosed herein. In some embodiments, the pharmaceutical composition has a delayed release period that overlaps the subject's normal period of sleep or being in a supine position. In some embodiments, the pharmaceutical composition is administered before the subject's normal sleep at night. In some embodiments, the pharmaceutical composition is administered less than 4 hours before bedtime, optionally less than 2 hours before bedtime. In some embodiments, the pharmaceutical composition is administered after the subject's normal waking time in the morning. In some embodiments, the pharmaceutical composition is administered to the subject in a supine position. In some embodiments, the subject's plasma level of desglymidodrine is at least about 3 ng/mL for a duration of about 4 hours to about 16 hours. In some embodiments, the subject's plasma level of desglymidodrine is at least about 3 ng/mL during waking hours of at least about 6 hours or at least about 14 hours.

The method of treatment may further include administering a single dose of a pharmaceutical composition that includes an active agent to the subject. The administration may be effective to cause an extended release of the active agent into the subject's plasma over an extended release period. The active agent may include one or more of: midodrine, a pharmaceutically acceptable salt of midodrine, desglymidodrine, a pharmaceutically acceptable salt of desglymidodrine, or a combination thereof. The single dose may be effective to provide a single rise in concentration of midodrine and/or desglymidodrine in the subject's plasma at the beginning of the extended release period.

In some embodiments, the single dose may be administered effective to raise blood pressure in the subject during the extended release period. The single dose may include the active agent in an amount in milligrams of about one of: 2.5, 3, 3.5, 4, 4.5, 5, 5.5, 6, 6.5, 7, 7.5, 8, 8.5, 9, 9.5, 10, 12.5, 15, 17.5, 20, 22.5, 25, 27.5, 30, 32.5, 35, 37.5, 40, 42.5, 45, 47.5, 50, 52.5, 55, 57.5, 60, 62.5, 65, 67.5, 70, 72.5, 75, 77.5, 80, 90, 100, 110, 120, 130, 140, and 150, e.g., about 30 milligrams, or a range between any two of the preceding values, for example, between about 2.5 milligrams and about 150 milligrams or between about 4 milligrams and about 50 milligrams.

In some embodiments, the pharmaceutical composition is an oral suspension and the dosage can be titrated to an effective level for the subject. A subject can start with an initial dose of the active and the subsequent doses can be adjusted based on the subject's response to the initial dose. Dose titration can be conveniently achieved for an oral suspension dosage form by adjusting the volume of oral suspension to be administered to the subject.

In some embodiments, the pharmaceutical composition has a delayed release period that overlaps the subject's normal period of sleep or being in a supine position. In some embodiments, the pharmaceutical composition is administered before the subject's normal sleep at night. In some embodiments, the pharmaceutical composition is administered less than 4 hours before bedtime, optionally less than 2 hours or less than 1 hour before bedtime. When the subject wakes up in the morning, the active agent is released from the pharmaceutical composition and the plasma concentration of the active agent reaches an effective level so that the subject can function normally. The pharmaceutical composition provides an extended release of the active agent and the subject does not need to take another dose during the day.

In some embodiments, the pharmaceutical composition is administered after the subject's normal waking time in the morning while the subject is still in a supine position. Because the pharmaceutical composition provides a delayed release period, e.g., for about 30 min, risk of supine hypertension is decreased or alleviated. After about 30 min or about 1 hour, when the active agent is released from the pharmaceutical composition and the subject feels the effect of the active agent, he can get up and function normally. The pharmaceutical composition provides an extended release of the active agent and the subject does not need to take another dose during the day.

In several embodiments, the method may include administering the single dose such that the single rise in concentration of desglymidodrine in the subject's plasma at the beginning of the extended release period. The method may include administering the single dose such that the extended release period substantially overlaps with the subject's waking hours, effective to raise blood pressure in the subject during the subject's waking hours.

The method may include administering the single dose to the subject according to any aspect of the pharmaceutical composition described herein. For example, the method may include administering the single dose to the subject in a dosage form including at least one of: a combined delayed release and extended release tablet; a plurality of particulates that are one of extended release and combined delayed release/extended release; the plurality of particulates configured for dispersal in a liquid carrier (or a suspending vehicle) suitable for oral administration. The method further may include combining the plurality of particulates with a liquid followed by oral administration to the subject; and the plurality of particulates dispersed in a liquid carrier suitable for oral administration.

In some embodiments, the method may include administering the single dose to the subject such that the extended release of the active agent into the subject's plasma over the extended release period is characterized by an extended release rate. The method may include administering the single dose to the subject such that greater than about 70% (w/w) of the active agent in the pharmaceutical composition is released to the subject over the extended release period. The extended release period may be, in hours, at least one of, or at least about one of: 4, 5, 6, 7, 8, 9, 10, 11, 12, 13, and 14, e.g., about 8 hours, or a range between any two of the preceding values, for example, of between about 4 hours and about 14 hours.

In various embodiments, the method may further include selecting the delayed-release form to provide the delayed-release period effective to cause the single rise in concentration of desglymidodrine in the subject's plasma at the beginning of the extended release period. In some embodiments, the single rise occurs within about ±30 minutes of the subject's normal time of waking and/or rising from a supine position. The delayed release period may be at least one of, or at least about one of: 0.25, 0.5, 1, 1.5, 2, 2.5, 3, 3.5, 4, 4.5, 5, 6, 7, 8, 9, 10, 11, and 12, e.g., at least about 0.5 hours, or a range between any two of the preceding values, for example, between about 0.25 hours and about 12 hours. The method may include, for example, releasing an amount of the active agent to the subject during the delayed release period, in percentage (w/w) of the total active agent in the pharmaceutical composition, of less than one of, or less than about one of: 5%, 4%, 3%, 2%, 1.5%, 1%, 0.75%, 0.5%, 0.25%, and 0.1%, e.g., less than about 4%. The method may include, for example, releasing the active agent to the subject during the delayed release period at a rate, in percentage (w/w) of the total active agent in the pharmaceutical composition per hour, of less than one of, or less than about one of: 5%, 4%, 3%, 2%, 1.5%, 1%, 0.75%, 0.5%, 0.25%, and 0.1%, e.g., less than about 4% per hour.

In one embodiment, the pharmaceutical composition, e.g., a tablet or a capsule, described herein is administered once or twice daily to a human subject in need thereof. In another embodiment, the pharmaceutical composition is administered once daily to a human subject in need thereof. The dose administered may be sufficient to obtain a suitable therapeutic response in the subject.

In one embodiment, this disclosure provides a method of treating orthostatic hypotension in a human subject in need thereof comprising administering to the human subject a pharmaceutical composition comprising:
  i. an effective amount of an active agent selected from midodrine, a pharmaceutically acceptable salt of midodrine, desglymidodrine, a pharmaceutically acceptable salt of desglymidodrine, or a combination thereof
  ii. an effective amount of a barrier coating agent or a delayed release agent to provide for a lag time of the active agent; and
  iii. a rate controlling agent, wherein the composition may be administered to a human subject in a supine position.

In one embodiment, the method comprises administering the composition comprising one or more rate controlling agents. In another embodiment, the one or more rate controlling agents are water-soluble, and/or water-insoluble, and/or water-permeable excipients.

In another embodiment, the release of the active agent from the composition is delayed for about 30 minutes. In another embodiment, no more than 10% of the active agent is released the first 30 minutes after administration. The delayed release period, is also referred to as lag time and is at least 30 minutes in the in vitro dissolution condition. The dissolution condition is 900 mL of 0.1 N HCl in USP apparatus I (basket) at 100 rpm. The examples of suitable acid-insoluble or water-impermeable agents include, but not limited to, water-insoluble, water permeable, water impermeable, or water soluble coating polymers such as methyl acrylate-methacrylic acid copolymers, cellulose acetate phthalate, hydroxypropyl methyl cellulose phthalate, hypromellose, ethyl cellulose, polyvinyl alcohol and any other suitable polymers that could be capable of achieving the said lag time in the said dissolution condition.

Methods of Administration and Dosage Forms

The present disclosure provides the dosage form(s) which can be taken in supine position. Dose administration in a supine position provides a significant advantage to patients, especially those whose orthostatic hypotension is in advanced stage.

The pharmaceutical composition described herein is in various dosage forms such as orally disintegrating tablets, mouth dissolving tablets, chewable tablets, buccal adhesive tablets, capsules, buccal adhesive films, sublingual tablets, oral suspension, and powder or granules for oral suspension. In another embodiment, the pharmaceutical composition is administered other than orally. Examples describe several such dosage forms in details including single layer tablets, bi-layer tablets, capsules, mutiparticulates, orally disintegrating tablets, oral suspensions etc. The dosage form comprises between about about 2.5 mg to about 150 mg or between about 4 milligrams and about 50 milligrams of the active agent. The amount of active agent may vary depending on the type of the dosage form.

The present disclosure also provides oral solid dosage forms which are administered with or without water at the time of administration. Examples of dosage forms which are administered without water include orally disintegrating tablets, chewable tablets, buccal adhesive tablets, and sublingual tablets. The advantages of these dosage forms are that the patients can take the desired dose without help while being in a supine position. Certain Examples herein specifically describe orally disintegrating tablets.

The present disclosure also provides oral solid dosage forms comprising a core or multiparticulates comprising an active agent selected from midodrine, a pharmaceutically acceptable salt of midodrine, desglymidodrine, a pharmaceutically acceptable salt of desglymidodrine, or a combination thereof and a barrier coating to provide for a delayed release of the active agent. Further, the oral dosage form optionally comprises one or more rate controlling agents for the extended release of the active agent.

In another embodiment, this disclosure provides an oral solid dosage form comprising an immediate release portion comprising an active agent selected from midodrine, a pharmaceutically acceptable salt of midodrine, desglymidodrine, a pharmaceutically acceptable salt of desglymidodrine, or a combination thereof and a barrier coating to provide for a delayed release of the active agent. Thus, the barrier coating delays release of the active agent from the dosage form. In one embodiment, the delay is of at least 30 minutes. In another embodiment, the delay is of at least 8 hours or at least 10 hours. The dosage form optionally comprises one or more additional coatings. The additional coatings can be a cosmetic coating. For example, a cosmetic film, which does not substantially change the release of the drug from the dosage form. A cosmetic film can be made from, for example, hydroxypropyl methylcellulose or wax. The cosmetic coating may also include a colorant.

The disclosed pharmaceutical compositions may be administered by any suitable route as described herein, including, for example, orally in tablets, capsules, or suspensions. In some embodiments, oral administration are exemplary modes of administration.

The disclosed compounds may be administered to the subject in conjunction with an acceptable pharmaceutical carrier as part of the described pharmaceutical compositions. Formulation of the compound to be administered may vary according to the route and vehicle of administration selected (e.g., capsule or tablet for ingestion, and the like). Suitable pharmaceutical carriers may contain inert ingredients that do not interact with the described compound. Standard pharmaceutical formulation techniques may be employed, such as those described in Remington's Pharmaceutical Sciences, 22nd ed., Mack Publishing Company, Easton, Pa., 2012. Methods for encapsulating compositions (such as in a coating of hard gelatin or cyclodextrin) or tableting compositions are known in the art (Baker, et al., "Controlled Release of Biological Active Agents," John Wiley and Sons, New York, 1986).

Dosage

In one embodiment, the pharmaceutical composition described herein is administered once or twice daily to a human subject in need thereof. In another embodiment, the pharmaceutical composition is administered once daily to a human subject in need thereof. The dose administered is sufficient to obtain a suitable therapeutic and/or prophylactic response in the subject. The dose varies based on the age and condition of the human subject to be treated. In one embodiment, the present disclosure provides pharmaceutical compositions comprising from about 2.5 mg to about 150 mg or about 4 mg to about 50 mg of the active agent. A pharmaceutical composition according to the present disclosure typically contains about 2.5 mg, 3 mg, 4 mg, 5 mg, 7.5 mg, 10 mg, 12.5 mg, 15, mg, 17.5 mg, 20 mg, 22.5 mg, 25 mg, 27.5 mg, 30 mg, 32.5 mg 35 mg, 37.5 mg, 40 mg, 42.5 mg, 45 mg, 47.5 mg, 50 mg, 52.5 mg, 55 mg, 57.5 mg, 60 mg, 62.5 mg, 65 mg, 67.5 mg, 70 mg, 72.5 mg, 75 mg, 77.5 mg, 80 mg, 82.5 mg, 85 mg, 87.5 mg, 90 mg, 100 mg, 110 mg, 120 mg, 130 mg, 140 mg, or 150 mg of the active agent. In one embodiment, the composition comprises 30 mg of the active agent.

Combination Therapy

The pharmaceutical compositions as disclosed herein may further comprise an additional active agent. The additional active agent may be any active drug substance that can be beneficially used with midodrine, a pharmaceutically acceptable salt thereof, desglymidodrine, or a pharmaceutically acceptable salt thereof. The non-limiting examples of such an additional active agent are hydrocortisone, fludrocortisone, octreotide and the like. The extended release pharmaceutical compositions disclosed herein can also be administered adjunctively with other active agents. By adjunctive administration is meant simultaneous administration of the compounds, in the same dosage form, simultaneous administration in separate dosage forms, or separate administration of the compounds.

As stated above, while the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art, having the benefit of the present application. Therefore, the application, in its broader aspects, is not limited to the specific details, illustrative examples shown, or any apparatus referred to. Departures may be made from such details, examples, and apparatuses without departing from the spirit or scope of the general inventive concept.

EXAMPLES

The disclosure is further illustrated by the following examples which are provided merely to be exemplary and do not limit the scope. Certain modifications and equivalents will be apparent to those skilled in the art and are intended to be included within the scope of the disclosure. The present disclosure provides, but is not limited to, the following formulation examples.

Example 1

Delayed Release/Extended Release Hydrophilic Core Tablets

Extended release tablets coated with a barrier coating agent are prepared as follows. Midodrine hydrochloride, a rate controlling agent and a filler and a lubricant are blended and then compressed into tablets, which are coated with the barrier coating agent. An example of this type of dosage form is shown below in Table 1.

TABLE 1

| Ingredient No. | Ingredient | Quantity (mg or % w/w) |
|---|---|---|
| | Extended Release Core | |
| 1 | Midodrine Hydrochloride | 4-50 mg or 2.5-150 mg |
| 2 | Hypromellose | 20-60% |
| 3 | Lactose Monohydrate | 0-60% |
| 4 | Talc | 0-2% |
| 5 | Magnesium Stearate | 0-2% |
| | Delayed Release Coating | |
| 6 | Methacrylic Acid-Ethyl Acrylate Copolymer (as dispersion) | 0-20% |

As an example, the following extended release hydrophilic core tablets coated with a coating agent to provide at least 30 minutes of lag time with little or no midodrine release after oral administration, are prepared as follows. Midodrine hydrochloride, hypromellose (METHOCEL K4M) and lactose monohydrate are blended and then lubricated with talc and magnesium stearate. The lubricated blend is then compressed using a 6 mm circular punch with a target weight of 120 mg. The tablets are then coated with aqueous dispersion of methacrylic acid-ethyl acrylate copolymer in a tablet coating machine. A specific example of this type of dosage form is shown below in Table 2.

TABLE 2

| Ingredient No. | Ingredient | mg/tablet |
|---|---|---|
| | Extended Release Core | |
| 1 | Midodrine Hydrochloride | 30.00 |
| 2 | Hypromellose (METHOCEL K4M) | 70.00 |
| 3 | Lactose Monohydrate | 18.20 |
| 4 | Talc | 1.20 |
| 5 | Magnesium Stearate | 0.60 |
| | TOTAL | 120.00 |
| | Delayed Release Coating | |
| 6 | Methacrylic acid-ethyl acrylate copolymer (as dispersion) | 12.00 |
| | TOTAL | 132.00 |

Example 2

Delayed Release/Extended Release Bi-Layer Tablets

Extended release bi-layer tablets coated with a barrier coating agent are prepared as follows. For the first layer, midodrine hydrochloride, a filler, and a lubricant are blended. For the second layer, midodrine hydrochloride, a rate controlling agent, and a filler are blended and then lubricated. The lubricated blend of both layers are compressed into a bilayer tablet, which is then coated with a barrier coating agent. An example of this type of dosage form is shown below in Table 3.

TABLE 3

| Ingredient No. | Ingredient | Quantity (mg or % w/w) |
|---|---|---|
| | Immediate Release 1st Layer | |
| 1 | Midodrine Hydrochloride | 0.4-5 mg or 2.5-150 mg |
| 2 | Microcrystalline Cellulose | 0-50% |
| 3 | Lactose Monohydrate | 0-30% |
| 4 | Talc | 0-2% |
| 5 | Magnesium Stearate | 0-2% |
| | Extended Release 2nd Layer | |
| 6 | Midodrine Hydrochloride | 3.6-45 mg |
| 7 | Hypromellose | 0-50% |
| 8 | Lactose Monohydrate | 0-30% |
| 9 | Talc | 0-2% |
| 10 | Magnesium Stearate | 0-2% |
| | Delayed Release Coating | |
| 11 | Methacrylic Acid-Ethyl Acrylate Copolymer (as dispersion) | 0-20% |

As an example, the following extended release hydrophilic core bi-layer tablets coated with a coating agent to provide at least 30 minutes of lag time with no release of midodrine after oral administration, are prepared as follows. For the first layer, midodrine hydrochloride, microcrystalline cellulose and lactose monohydrate are blended and then lubricated with talc and magnesium stearate. For the second layer, midodrine hydrochloride, hypromellose (METHOCEL K4M) and lactose monohydrate are blended and then lubricated with talc and magnesium stearate. The lubricated blend of both the layers are then compressed in to a bilayer tablet using a 6.5 mm circular punch with a target weight of 130 mg. The bilayer tablets are then coated with aqueous dispersion of methacrylic acid-ethyl acrylate copolymer in a tablet coating machine. A specific example of this type of dosage form is shown below in Table 4.

TABLE 4

| Ingredient No. | Ingredient | mg/tablet |
|---|---|---|
| Immediate Release 1st Layer | | |
| 1 | Midodrine Hydrochloride | 9.00 |
| 2 | Microcrystalline Cellulose | 21.40 |
| 3 | Lactose Monohydrate | 9.00 |
| 4 | Talc | 0.40 |
| 5 | Magnesium Stearate | 0.20 |
| | TOTAL | 40.00 |
| Extended Release 2nd Layer | | |
| 1 | Midodrine Hydrochloride | 21.00 |
| 2 | Hypromellose (Methocel K4M) | 49.00 |
| 3 | Lactose Monohydrate | 18.50 |
| 4 | Talc | 1.00 |
| 5 | Magnesium Stearate | 0.50 |
| | TOTAL | 90.00 |
| Bilayer Core | | |
| | TOTAL | 130.00 |
| Delayed Release Coating | | |
| | Methacrylic Acid-Ethyl Acrylate Copolymer (as dispersion) | 13.00 |
| | TOTAL | 143.00 |

Example 3

Multiparticulates with Combined Extended Release/Delayed Release Coating

An extended release formulation is prepared by high shear granulation, extrusion and spheronization process to produce midodrine hydrochloride loaded multiparticulates, which are then coated with a rate controlling agent and a barrier coating in a fluid bed processor. An example of this type of dosage form is shown below in Table 5.

TABLE 5

| Ingredient No. | | Ingredient | Quantity (mg or % w/w) |
|---|---|---|---|
| 1 | Multiparticulates | Midodrine Hydrochloride | 4-50 mg or 2.5-150 mg |
| 2 | | Microcrystalline Cellulose | 0-80% |
| 3 | | Hypromellose | 0-20% |
| 4 | | Water | q.s. |
| 5 | Extended Release Coating | Ethylcellulose | 0-15% |
| 6 | | Hypromellose | 0-10% |
| 7 | | Ethanol/Water | q.s. |
| 8 | Delayed Release Coating | Ethylcellulose (as dispersion) | 0-10% |

An oral suspension comprising extended release multiparticulate systems coated with a barrier coating agent to provide a lag time of at least 30 mins after oral administration, is prepared. The oral suspension can be in the form of ready-to-use or being reconstituted before use. A suspension gives a great advantage to patients, especially geriatric and pediatric patients, and enable them to take medicine in a supine position.

As an example, the following extended release formulation is prepared by high shear granulation, extrusion and spheronization process to produce the drug loaded cores, which are then coated with an extended release coating and a lag time coating. The active midodrine hydrochloride and a filler are dry blended in a high shear granulator for 1-5 minutes, and then a binder solution is added to produce wet mass, followed by extrusion in an extruder. The extrudates are then loaded into a spheronizer and spherical shaped pellets are formed, which are then dried and coated with extended release coating in a fluid bed processor. A delayed release coating layer is applied afterwards to produce bi-layered pellets and filled into capsules or sachets. A specific example of this type of dosage form is shown below in Table 6.

TABLE 6

| Extended Release Coating | | |
|---|---|---|
| | Ingredient | mg/tablet |
| Core | Midodrine hydrochloride | 30 mg |
| | Microcrystalline Cellulose | 60 mg |
| | Hypromellose | 10 mg |
| Extended release coating | Ethylcellulose | 9 mg |
| | Hypromellose | 3 mg |
| Delayed Release Coating | Ethylcellulose (as dispersion) | 5.6 mg |
| | Total | 117.6 mg |

Example 4

Lipid Multiparticulates for Delayed Release/Extended Release

An extended release formulation can be prepared by hot melt spraying or melt granulation process to produce drug loaded extended release multi-particulates, which are then coated with a delayed release layer. The active agent, midodrine HCL is mixed with a lipid based excipient, which is melted into semi-solid or liquid forms during the melt granulation process to produce the lipid multi-particulates. A sub-coat ranging from 1-5% may be applied to make a smoother surface for the following delayed release coating in a fluid bed processor. An example of this type of dosage form is shown below in Table 7.

TABLE 7

| Ingredient No. | | Ingredient | Quantity (mg or % w/w) |
|---|---|---|---|
| 1 | Extended Release | Midodrine Hydrochloride | 4-50 mg or 2.5-150 mg |
| 2 | Matrix | Glycerol Dibehenate | 0-40% |
| 3 | Multiparticulates | Microcrystalline Cellulose | 0-50% |
| 4 | | Poloxamer 407 | 0-5% |
| 5 | Sub-coat | Hypromellose | 0-3% |
| 6 | | Purified Water | q.s. |
| 7 | Delayed Release Coating | Hypromellose Phthalate | 0-10% |
| | | Triethyl Citrate | 0-1.5% |
| 8 | | Isopropanol/Water | q.s. |

As an example, the following extended release formulation is prepared by hot melt spraying or melt granulation process to produce drug loaded extended release matrix cores, which are then coated with a delayed release coating. The active midodrine hydrochloride is coated with a lipid based excipient which is melted into a waxy form during the granulation process and then blended with a filler and dissolution enhancer to produce the lipid multiparticulates in a blender. A sub-coat ranges from 1-5% can be applied then to make a smoother surface for the following barrier coating in a fluid bed processor. A specific example of this type of dosage form is shown below in Table 8.

TABLE 8

| # | Ingredient | | Quantity (mg) |
|---|---|---|---|
| 1 | Extended release | Midodrine HCL | 30 mg |
| 2 | Matrix Core | Glycerol dibehenate | 25 mg |
| 3 | 100 mg | Microcrystalline cellulose | 40 mg |
| 4 | | Poloxamer 407 | 5 mg |
| 5 | Sub-coat 3% | Hypromellose | 3 mg |
| 6 | | Purified water | q.s. |
| 7 | Delayed release coating | Hypromellose phthalate | 9.5 mg |
| 8 | | Triethyl citrate | 0.8 mg |
| 9 | | Ethanol/water | q.s. |
| | Total | | 113.3 mg |

Example 5

Hydrophilic Matrix Multi-Particulates for Delayed Release/Extended Release

An delayed extended release formulation is prepared by a granulation, extrusion and spheronization process to form the hydrophilic matrix multiparticulates, followed by application of a delayed release coating in a fluid bed processor. An example of this type of dosage form is shown in Table 9.

TABLE 9

| Ingredient No. | Ingredient | | Quantity (mg or % w/w) |
|---|---|---|---|
| 1 | Extended Release Matrix | Midodrine Hydrochloride | 4-50 mg or 2.5-150 mg |
| 2 | Multiparticulates | Hypromellose | 0-40% |
| 3 | | Microcrystalline Cellulose | 0-50% |
| 4 | | Polyvinyl Pyrrilidone | 0-10% |
| 5 | | Purified Water | q.s. |
| 6 | Barrier Coating | Hypromellose Phthalate | 0-15% |
| 7 | | Triethyl Citrate | 0-1% |
| 8 | | Isopropanol/Water | q.s. |

As an example, the following delayed and extended release formulation is prepared using matrix multi-particulates and a delayed release coating. A specific example of this type of dosage form is shown below in Table 10.

TABLE 10

| # | Ingredient | | Quantity (mg) |
|---|---|---|---|
| 1 | Extended release | Midodrine HCL | 30 mg |
| 2 | Matrix Core | Hypromellose | 30 mg |
| 3 | | Microcrystalline cellulose | 35.7 mg |
| 4 | | Polyvinyl pyrrolidine | 5 mg |
| 5 | | Purified water | q.s. |
| 6 | Delayed release coating | Hypromellose phthalate | 9.5 mg |
| 7 | | Triethyl citrate | 0.8 mg |
| 8 | | Ethanol/water | q.s. |
| | Total | | 111 mg |

Example 6

Drug Layered Multiparticulates for Delayed Release/Extended Release

A delayed and extended release formulation is prepared by spraying the drug solution or suspension onto pharmaceutically inert cores and coated with an extended release composition, followed by application of a delayed release coating in a fluid bed processor. An example of this type of dosage form is shown below in Table 11.

TABLE 11

| # | Ingredients | | Quantity (mg or % w/w) |
|---|---|---|---|
| 1 | Inert core | Sugar spheres | 0-80% |
| 2 | Drug layer | Midodrine HCL | 4-50 mg or 2.5-150 mg |
| 3 | | Hypromellose | 0-10% |
| 4 | | Purified water | q.s. |
| 5 | Extended release multi-particulates | Ethyl cellulose | 0-25% |
| 6 | | Hypromellose | 0-10% |
| 7 | | Ethanol/water | q.s. |
| 8 | Delayed release coating | ethyl cellulose (as dispersion) | 0-10% |
| 9 | | Purified water | q.s. |

An example of how the multi-particulates are prepared is shown below. The active agent, midodrine HCl, is dissolved in water with a binder to prepare a solution. The solution is sprayed onto a pharmaceutically inert core (e.g., sugar microspheres or microcrystalline cellulose microspheres) and dried in a fluid bed processor. Alternatively, the active agent may be applied through powder layering or suspension spraying to the pharmaceutically inert core. A mixture of a film forming agent such as ethyl cellulose and a pore former such as hypromellose or hydroxypropyl cellulose may be applied. Different drug release rates can be obtained by adjusting the molecular weight/viscosity of the film forming agent and/or change the ratio between film forming agent and pore former. A delayed release coating may be applied to the coated drug layered multi-particulates in a fluid bed processor. A specific example of this type of dosage form is shown below in Table 12.

TABLE 12

| # | Ingredients | | Quantity (mg) |
|---|---|---|---|
| 1 | Inert core | Sugar spheres | 260 mg |
| 2 | Drug layer | Midodrine HCL | 30 mg |
| 3 | | Hypromellose | 10 mg |
| 4 | | Purified water | q.s. |

TABLE 12-continued

| # | Ingredients | | Quantity (mg) |
|---|---|---|---|
| 5 | Extended release coating | Ethyl cellulose | 24 mg |
| 6 | | Hypromellose | 6 mg |
| 5 | | Isopropanol/purified water | q.s. |
| 6 | Delayed release coating | Ethyl cellulose (as dispersion) | 16.5 mg |
| 7 | | Purified water | q.s. |
| | | Total | 346.5 mg |

Example 7

Orally Disintegrating Tablet Containing Extended Release Multiparticulates

An orally disintegrating tablet comprising extended release multiparticulate systems is designed to disintegrate rapidly on contact with saliva and enable oral administration without water or chewing, which is advantageous to patients when taking the medication in a supine position.

An inert core can be used and midodrine hydrochloride solution is sprayed onto the core. The drug layered multiparticulates are then coated with a rate controlling agent in a fluid bed processor, which are then blended with a filler, a disintegrant and a lubricant, and compressed into orally disintegrated tablets. An example of this type of dosage form is shown below in Table 13.

TABLE 13

| # | Ingredients | | Quantity (mg or % w/w) |
|---|---|---|---|
| 1 | Inert core | Sugar spheres | 0-40% |
| 2 | Drug layer | Midodrine HCL | 4-50 mg or 2.5-150 mg |
| 3 | | Hypromellose | 0-5% |
| 4 | | Purified water | q.s. |
| 5 | Extended release multi- | Ethyl cellulose | 0-30% |
| 6 | particulates | Hypromellose | 0-5% |
| 7 | | Ethanol/water | q.s. |
| 8 | Delayed release coating | ethyl cellulose (as dispersion) | 0-10% |
| 9 | | Purified water | q.s. |
| 10 | Other excipients | Mannitol | 0-60% |
| 11 | | Croscarmellose sodium | 0-10% |
| 12 | | Colloidal silicon dioxide | 0-2% |
| 13 | | Peppermint flavor | 0-3% |
| 14 | | Magnesium stearate | 0-2% |

As an example, the following orally disintegrating tablet is prepared. The active midodrine hydrochloride is blended with hypromellose and then mixed with a filler and a binder in a high shear granulator to produce the wet mass. The wet mass is then extruded and spheronized into pellets, dried and coated in a fluid bed with a delayed release coating. Next the coated pellets are blended with a filler, a lubricant and a disintegrant and compressed gently into orally disintegrated tablets. A specific example of this type of dosage form is shown below in Table 14.

TABLE 14

Orally disintegrating Tablet Containing Multiparticulates

| Inert Core | Sugar Spheres | 160 mg |
|---|---|---|
| Drug layer | Midodrine hydrochloride | 30 mg |
| | Hypromellose | 10 mg |
| Extended Release Coating | Ethylcellulose | 24 mg |
| | Hypromellose | 6 mg |
| Delayed release coating | Ethylcellulose (as dispersion) | 16.5 mg |
| | Total | 246.5 mg |
| | Microcrystalline Cellulose | 219 mg |
| | Croscarmellose Sodium | 20 mg |
| | Colloidal Silicon Dioxide | 12.5 mg |
| | Magnesium Stearate | 2 mg |
| | Total | 500 mg |

Example 8

Delayed and Extended Release Tablets with Different Delayed Periods

A tablet with an extended release core and an outer delayed release coating is prepared as shown in Tables 15-18 (Formulations 1A-1D). For the extended release drug core, a filler, a rate controlling agent and a binder are mixed with the drug in a high shear granulator for 5 mins, then sprayed with water and granulated. The granules are dried in an oven at 70° C. for 1 hour and sieved through a 25-mesh screen. Sieved granules are lubricated with magnesium stearate and compressed with a tablet press at the compression force 100 kPa. Tablets are round concave shape at size 9 mm, which are coated with a mixture of SURELEASE and OPADRY dispersion in a tablet coating machine.

All formulations contain 30 mg of midodrine HCl but vary in the amount of the delayed release coating agents (i.e. SURELEASE and OPADRY dispersion), which provide different delayed release periods. Ratio between the film forming agent (e.g. SURELEASE) and pore former (e.g. OPADRY) can also be adjusted to obtain different delayed time.

TABLE 15

Formulation 1A

| # | Ingredients | Quantity (mg) |
|---|---|---|
| | Extended release core | |
| 1 | Midodrine HCL | 30 mg |
| 2 | Microcrystalline cellulose | 155 mg |
| 3 | Hypromellose | 155 mg |
| 4 | Polyvinyl pyrrolidine | 10 mg |
| 5 | Magnesium Stearate | 2 mg |
| 6 | Purified water | q.s. |
| | Delayed release coating 4% | |
| 7 | Opadry | 2.8 mg |
| 8 | Surelease dispersion | 11.2 mg |
| 9 | Purified water | q.s. |
| | Total | 366 mg |

TABLE 16

Formulation 1B

| # | Ingredients | Quantity (mg) |
|---|---|---|
| | Extended release core | |
| 1 | Midodrine HCL | 30 mg |
| 2 | Microcrystalline cellulose | 155 mg |
| 3 | Hypromellose | 155 mg |
| 4 | Polyvinyl pyrrolidine | 10 mg |
| 5 | Purified water | q.s. |
| | Delayed release coating 6% | |
| 6 | Opadry | 4.20 mg |
| 7 | Surelease dispersion | 16.80 mg |
| 8 | Purified water | q.s. |
| | Total | 371 mg |

TABLE 17

Formulation 1C

| # | Ingredients | Quantity (mg) |
|---|---|---|
| | Extended release core | |
| 1 | Midodrine HCl | 30 mg |
| 2 | Microcrystalline cellulose | 155 mg |
| 3 | Hypromellose | 155 mg |
| 4 | Polyvinyl pyrrolidine | 10 mg |
| 5 | Magnesium Stearate | 2 mg |
| 6 | Purified water | q.s. |
| | Delayed release coating 8% | |
| 7 | Opadry | 5.6 mg |
| 8 | Surelease dispersion | 22.4 mg |
| 9 | Purified water | q.s. |
| | Total | 380 mg |

TABLE 18

Formulation 1D

| # | Ingredients | Quantity (mg) |
|---|---|---|
| | Extended release core | |
| 1 | Midodrine HCL | 30 mg |
| 2 | Microcrystalline cellulose | 155 mg |
| 3 | Hypromellose | 155 mg |
| 4 | Polyvinyl pyrrolidine | 10 mg |
| 5 | Magnesium Stearate | 2 mg |
| 6 | Purified water | q.s. |
| | Delayed release coating 20% | |
| 7 | Opadry | 14.0 mg |
| 8 | Surelease dispersion | 56.0 mg |
| 9 | Purified water | q.s. |
| | Total | 422 mg |

Figure 5:
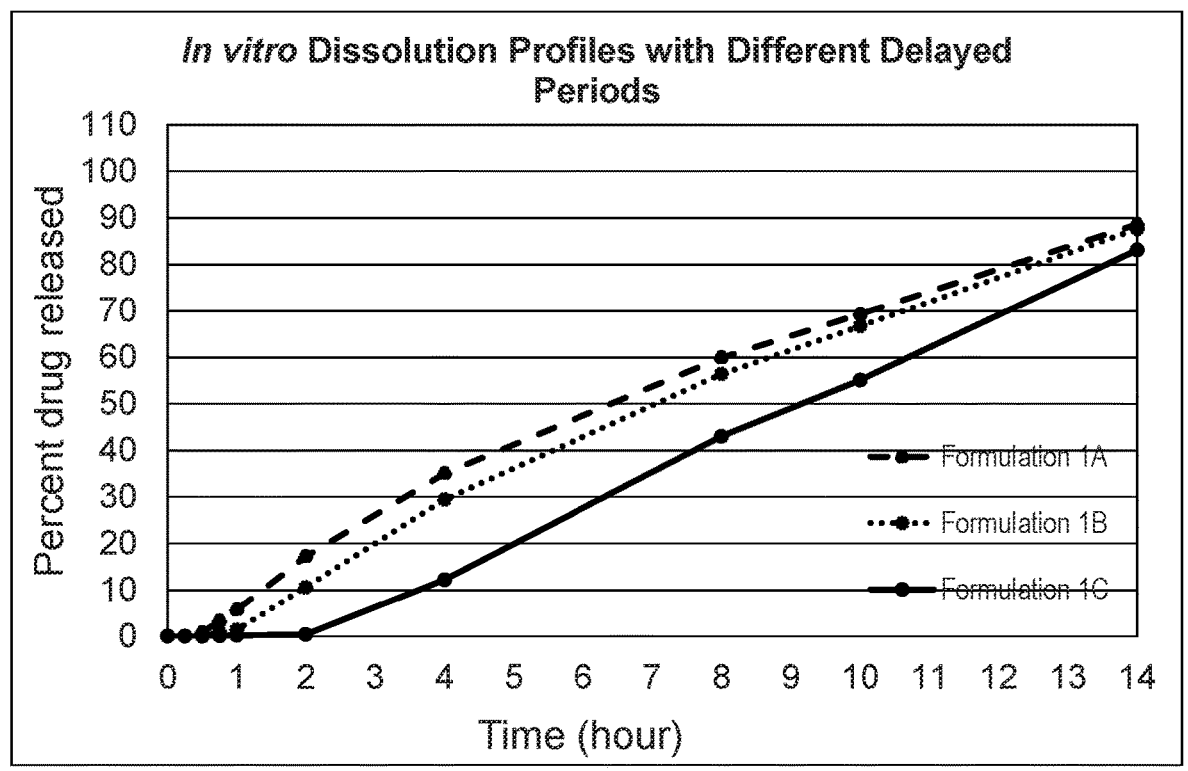
FIG. 5 is a graph of in vitro release profiles of exemplary pharmaceutical formulations 1A, 1B, and 1C as provided in Example 8, showing a delayed release period of about 30 minutes up to 2 hours and an extended release period of about 10 hours.
Figure 6:
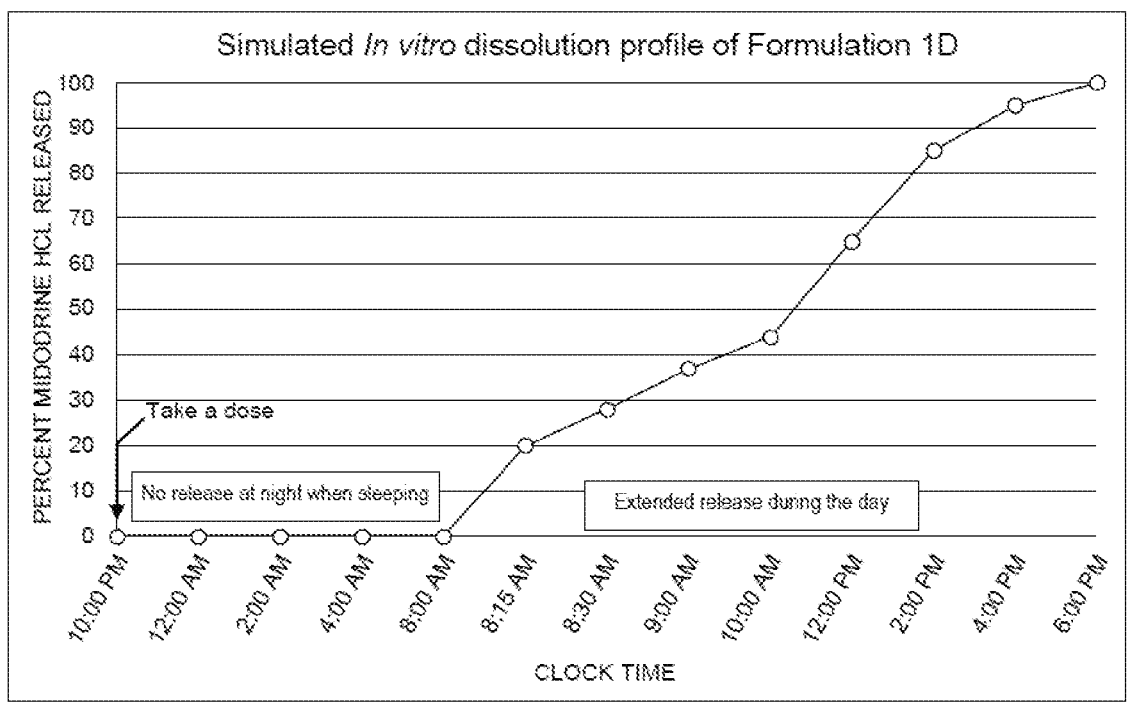
FIG. 6 is a graph of a simulated in vitro release profile of an exemplary pharmaceutical formulation 1D as provided in Example 8, showing a delayed release period of about 10 hours and an extended release period of about 10 hours after the delay period.

The delayed release portion of the profile may be characterized by a release of no active agent or no more than 1% or 5% or 10% w/w of the active agent within a period after the start of an in vitro dissolution test as shown in FIG. 5, FIG. 6 and Table 19 below.

TABLE 19

Dissolution Profiles of the Marketed IR Tablet and DR + ER Formulations
Dissolution Condition
900 mL 0.1N HCL (pH 1.2)
USP I (Basket) at 100 rpm

| Time (hour) | Marketed IR Tablet (5 mg) [1] | Formulation 1A (30 mg) | Formulation 1B (30 mg) | Formulation 1C (30 mg) | Formulation 1D (30 mg) [2] |
|---|---|---|---|---|---|
| 0 | 0.0 | 0.0 | 0.0 | 0.0 | 0.0 |
| 0.25 | 100.7 | 8.1 | 0.0 | 0.0 | 0.0 |
| 0.5 | 100.8 | 17.9 | 0.8 | 0.0 | 0.0 |
| 0.75 | 100.9 | 21.3 | 3.3 | 0.1 | 0.0 |
| 1 | NA | 24.6 | 5.7 | 0.2 | 0.0 |
| 2 | NA | 38.2 | 17.2 | 0.4 | 0.1 |
| 4 | NA | 56.3 | 35.0 | 12.2 | 0.5 |
| 8 | NA | 78.0 | 59.9 | 43.0 | 1.2 |
| 10 | NA | 85.8 | 69.3 | 55.1 | 4.8 |
| 14 | NA | 93.6 | 88.6 | 83.1 | 45.4 |
| 18 | NA | NA | NA | NA | 80.2 |
| 24 | NA | NA | NA | NA | 100.0 |

[1] For IR tablet, there expected no difference in in vitro dissolution profile between 5 mg and 10 mg dose.
[2] Simulated in vitro dissolution profile. The rest of the table contains actual data.
"NA" means not applicable.

The above formulations, prepared from components as shown in Table 15-18, may show a delayed release time of about 30 minutes (Formulation 1A) to about 10 hours (Formulation 1D) after the start of an in vitro dissolution test. Such delayed release of the active agent may allow administration of the drug to patients in a supine position. Moreover, as the time of delayed release is further prolonged to 10 hours (Formulation 1D in Table 18), the patient may be able to take the medication at night around 10:00 PM and then go to sleep. There is no (or less than 1%) drug release for 10 hours during this bedtime. When the patient gets up in the morning, e.g., at around 8:00 AM, the drug starts releasing for an extended period, e.g. 10 hours, during the day until fully released in the evening, e.g. 6:00 PM.

Example 9

Delayed Release/Extended Release Compressed Tablet for Gastric Retention by Size Pharmaceutically acceptable gastric fluid-swellable compositions may swell upon contact with gastric fluid and may maintain physical integrity in a swollen state in the stomach. Pores may be incorporated into the tablet to achieve rapid swelling before the stomach is emptied. Delayed release/extended release particulates that delay drug release in the acidic stomach environment may be mixed with the gastric fluid-swellable composition and compressed into tablets. After administration of the tablet, the gastric fluid-swellable composition may swell rapidly such that the size of the tablet is greater than the diameter of a subject's pyloric sphincter, thus retaining the tablet in the stomach up to, e.g., 8-10 hours.

Tablets containing drug-loaded extended release multi-particulates can be prepared by layering the drug onto microcrystalline cellulose spheres and coated with rate controlling agents. These multi-particulates are further coated by a delayed release layer preventing the drug from releasing during the retention time in stomach. After coating, multi-particulates are blended with a lubricant, a filler and the excipient that swells in stomach, and compressed into tablets. Such delayed release/extended release compressed tablets may be prepared as shown in Table 20.

TABLE 20

| # | Ingredients | | Quantity (mg) |
|---|---|---|---|
| 1 | Extended release multi-particulates | Midodrine HCL | 30 mg |
| 2 | | Microcrystalline cellulose spheres | 30 mg |
| 3 | | Ethyl cellulose | 5.76 mg |
| 4 | | Hypromellose | 1.44 mg |
| 5 | | Isopropanol alcohol | q.s. |
| 6 | | Purified water | q.s. |
| 7 | Delayed coating layer | Eudragit L30D-55 | 10.80 mg |
| 8 | | Purified water | q.s. |
| 9 | Other Excipients | Hypromellose | 20 mg |
| 10 | | Silicified microcrystalline cellulose | 50 mg |
| 11 | | Polyethylene oxide | 60 mg |
| 12 | | Magnesium stearate | 1 mg |
| | Total | | 209 mg |

Example 10

Delayed Release/Extended Release Compressed Tablet for Gastric Retention by Density Another type of gastric retention delivery system utilizes buoyancy or density change of the dosage form in gastric fluid. Such a system may be prepared by incorporating an excipient into the dosage that swells and a component (such as an effervescent agent) within the swollen dosage that generates gas in contact with gastric fluid and causes the bulk density of the dosage reduced to less than the density of gastric fluid. An example of the component generating gas is sodium bicarbonate which releases carbon dioxide in contact with gastric acid. The carbon dioxide is trapped within the swollen tablet or beads, which lower its overall density, causing the tablet or beads to float in stomach. A formulation example is shown below in Table 21

TABLE 21

| # | Ingredients | | Quantity (mg) |
|---|---|---|---|
| 1 | Extended release multi-particulates | Midodrine HCL | 30 mg |
| 2 | | Microcrystalline cellulose spheres | 30 mg |
| 3 | | Ethyl cellulose | 5.76 mg |
| 4 | | Hypromellose | 1.44 mg |
| 5 | | Isopropanol alcohol | q.s. |
| 6 | | Purified water | q.s. |
| 7 | Delayed release coating | Eudragit L30D-55 | 10.80 mg |
| 8 | | Purified water | q.s. |
| 9 | Other excipients | Silicified microcrystalline cellulose | 90 mg |
| 10 | | Hypromellose | 50 mg |
| 11 | | Sodium bicarbonate | 30 mg |
| 12 | | Magnesium stearate | 2 mg |
| | Total | | 250 mg |

Example 11

Delayed Release/Extended Release Formulations for Gastric Retention by Mucoadhesion Mucoadhesive drug delivery system is designed that the dosage form becomes hydrated and sticky once in contact with gastric fluid and can attach onto the lumen of stomach wall and stay there for a long period. Excipients such as sodium carboxymethyl cellulose, Carbopol, chitosan, and lectin are this kind and can be used in this formulation. Mucoadhesive delivery system can be in different dosage forms, e.g. tablets, pellets, and capsules. An example of a mucoadhesive tablet that enables gastric retention is shown below Table 22.

TABLE 22

| # | Ingredients | | Quantity (mg) |
|---|---|---|---|
| 1 | Extended release multi-particulates | Midodrine HCL | 30 mg |
| 2 | | Sugar spheres | 30 mg |
| 3 | | Ethyl cellulose | 5.76 mg |
| 4 | | Hypromellose | 1.44 mg |
| 5 | | Isopropanol alcohol | q.s. |
| 6 | | Purified water | q.s. |
| 7 | Delayed release coating | Eudragit L30D-55 | 10.80 mg |
| 8 | | Purified water | q.s. |
| 9 | Other excipients | Silicified microcrystalline cellulose | 30 mg |
| 10 | | Hypromellose | 50 mg |
| 11 | | Sodium carboxymethyl cellulose | 50 mg |
| 12 | | Magnesium stearate | 2 mg |
| | Total | | 210 mg |

Example 12

Delayed Release/Extended Release Formulations for Gastric Retention by a Combination of Different Mechanisms A combination of floating, swelling or mucoadhesion mechanisms may improve gastric retention property of the delivery system. Below is an example of the delivery system showing both swelling and floating behaviors to retain the dosage in stomach. Delayed and extended release multi-particulates are prepared and filled into a capsule. The capsules are coated with a gastric swelling component together with a gas generating excipient. Once in stomach, the swelling component forms a thick gel layer and the capsule becomes larger in size than the pyloric sphincter of the subject, while the gas generating excipient releases carbon dioxide which are trapped within the gel layer causing the dosage to float. An example of this type of dosage form is shown below in Table 23.

TABLE 23

| # | Ingredients | | Quantity (mg) |
|---|---|---|---|
| 1 | Extended release multi-particulates | Midodrine HCL | 30 mg |
| 2 | | Microcrystalline cellulose spheres | 30 mg |
| 3 | | Ethyl cellulose | 5.76 mg |
| 4 | | Hypromellose | 1.44 mg |
| 5 | | Isopropanol alcohol | q.s. |
| 6 | | Purified water | q.s. |
| 7 | Delayed release coating | Eudragit L30D-55 | 10.80 mg |
| 8 | | Purified water | q.s. |
| 9 | Other excipients | Polyethylene oxide | 60 mg |
| 10 | | Hypromellose | 40 mg |

TABLE 23-continued

| # | Ingredients | Quantity (mg) |
|---|---|---|
| 11 | Sodium bicarbonate | 20 mg |
| 12 | Talc | 2 mg |
|  | Total | 200 mg |

Example 13

Delayed and Extended Release Hydrophobic Tablets

Delayed and extended release hydrophobic tablets are prepared by preparing an extended release core with a hydrophobic rate controlling agent such as hydrogenated castor oil, followed by applying a delayed release coating. An example of this type of dosage form is shown below in Table 24.

TABLE 24

| # | Ingredient | Quantity (mg or % w/w) |
|---|---|---|
|  | Extended release Core |  |
| 1 | Midodrine HCL | 2.5-150 mg |
| 2 | Hydrogenated castor oil | 0-40% |
| 3 | Microcrystalline cellulose | 0-60% |
| 4 | Talc | 0-2% |
| 5 | Magnesium stearate | 0-2% |
|  | Delayed release coating |  |
| 6 | Methacrylic acid-ethyl acrylate Copolymer (as dispersion) | 0-40% |
| 7 | Purified water | q.s. |

Extended release hydrophobic tablets with a 30 minutes' delayed release coating are prepared as follows. Midodrine HCl, hydrogenated castor oil, microcrystalline cellulose and talc are blended and lubricated with magnesium stearate. The lubricated blend is compressed using a 6 mm circular punch with a target weight of 120 mg. After compression, the tablets are coated with an aqueous dispersion of methacrylic acid-ethyl acrylate copolymer in a tablet coating machine for delayed release function. A specific example is shown below in Table 25.

TABLE 25

| # | Ingredient | mg/tablet |
|---|---|---|
|  | Extended release core |  |
| 1 | Midodrine HCL | 30 mg |
| 2 | Hydrogenated castor oil | 30 mg |
| 3 | Microcrystalline cellulose | 58.2 mg |
| 4 | Talc | 1.2 mg |
| 5 | Magnesium Stearate | 0.6 mg |
|  | Delayed release coating |  |
| 6 | Methacrylic acid-ethyl acrylate copolymer (as dispersion) | 12 mg |
| 7 | Purified water | q.s. |
|  | TOTAL | 132 mg |

Example 14

Delayed and Extended Release Multi-Particulate Suspension

An oral suspension comprising the multi-particulate systems described above (Examples 4-6) can be prepared as a ready-to-use suspension or sachet/packet for reconstitution by adding a suspending vehicle (either in liquid or in solid form) into the formulation. A suspension may provide advantageous or convenient dosage for flexible dosing, dose titration, and is easy for the patient to swallow. An example of the suspension is shown below in Table 26.

TABLE 26

| # |  | Ingredients | Quantity (mg) |
|---|---|---|---|
| 1 | Drug loaded core | Midodrine HCL | 30 mg |
| 2 |  | Microcrystalline cellulose | 60 mg |
| 3 |  | Polyvinyl pyrrolidinone | 10 mg |
| 4 |  | Purified water | q.s. |
| 5 | Extended release coating | Ethyl cellulose | 9 mg |
| 6 |  | Hypromellose | 3 mg |
| 7 |  | Isopropanol/water | q.s. |
| 8 | Delayed release coating | Ethyl cellulose (as dispersion) | 5.6 mg |
| 9 |  | Purified water | q.s. |
| 10 | Suspending vehicle | Mannitol | 80 mg |
| 11 |  | Peppermint flavor | 5 mg |
| 12 |  | Sucrose | 20 mg |
| 13 |  | Xanthan gum | 6 mg |
| 14 |  | Sodium lauryl sulfate | 1.4 mg |
|  |  | Total | 230 mg |

Example 15

Delayed and Extended Release Formulation with Immediate Release Component

Delayed and extended release formulations enable delivery of the medication to the patients when they are in supine position. An immediate release component of the drug can also be incorporated into the formulation and provide an initial fast release of the drug. This helps quickly relieve any symptoms the patient is suffering. To avoid supine hypertension, which is a risk of taking midodrine HCl, immediate release component of the drug needs to be coated with a delayed release layer, protecting it from releasing for a period, e.g. 30 minutes up to 10 hours, so that the patient can take the medication in supine position or at night before bedtime.

The immediate release component containing the active drug can comprise up to 20%, or up to 30%, or up to 40%, or up to 50%, or up to 60% of the whole dose that the patient is required to take during a day, with the rest of the dose being the extended release component. Immediate release component can be in the form of powder, granules, pellets, a drug layer, or any pharmaceutically acceptable forms. Several examples of the immediate release and extended release combination formulation are given below.

A. Bilayer Tablet

Bilayer tablets containing an immediate release drug layer and an extended release layer can be prepared as follows. The drug, a filler, and a binder are blended in a high shear granulator for a few minutes until a uniform blend is formed. Water is sprayed into the blend and materials are granulated for a few minutes. Wet granules formed in the wet granulation process are then dried in a fluid bed processor or in an oven. Dried granules can be split into two portions, of which 20% can be used for the immediate release layer of the tablet, with the rest 80% of the granules being further blended with a release controlling agent and used for the extended release layer. Both granules are lubricated before being compressed into bilayer tablets. Bilayer tablets are then coated with a delayed release component. An example of the formulation is shown below in Table 27.

TABLE 27

| # | Ingredients | Quantity (mg) |
|---|---|---|
| | Immediate release layer | |
| 1 | Midodrine HCL | 6 mg |
| 2 | Microcrystalline cellulose | 30 mg |
| 3 | Polyvinyl pyrrolidine | 1.4 mg |
| 4 | Magnesium stearate | 0.2 mg |
| 5 | Purified water | q.s. |
| | Extended release layer | |
| 6 | Midodrine HCL | 24 mg |
| 7 | Microcrystalline cellulose | 120 mg |
| 8 | Polyvinyl pyrrolidine | 5.6 mg |
| 9 | Purified water | q.s. |
| 10 | Hypromellose | 120 mg |
| 11 | Magnesium stearate | 1.4 mg |
| | Delayed release coating | |
| 12 | Hypromellose | 3.7 mg |
| 13 | Ethyl cellulose (as dispersion) | 14.8 mg |
| 14 | Purified water | q.s. |
| | Total | 327.1 mg |

B. Multi-Particulates

Figure 7:
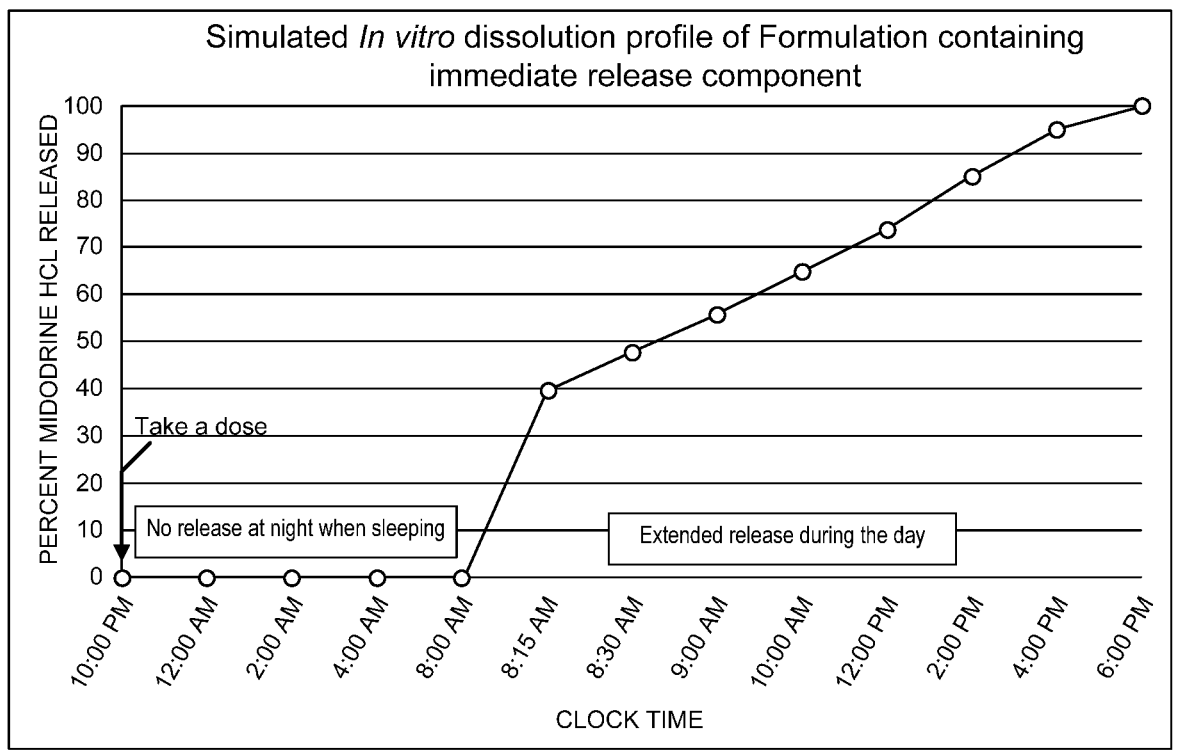
FIG. 7 is a graph of a simulated in vitro release profile of an exemplary pharmaceutical composition containing an immediate release drug component as provided in Example 15, Table 28, showing a delayed release period of about 10 hours followed by an immediate 40% drug release within 15 minutes and an extended release period of about 10 hours.
Figure 8:
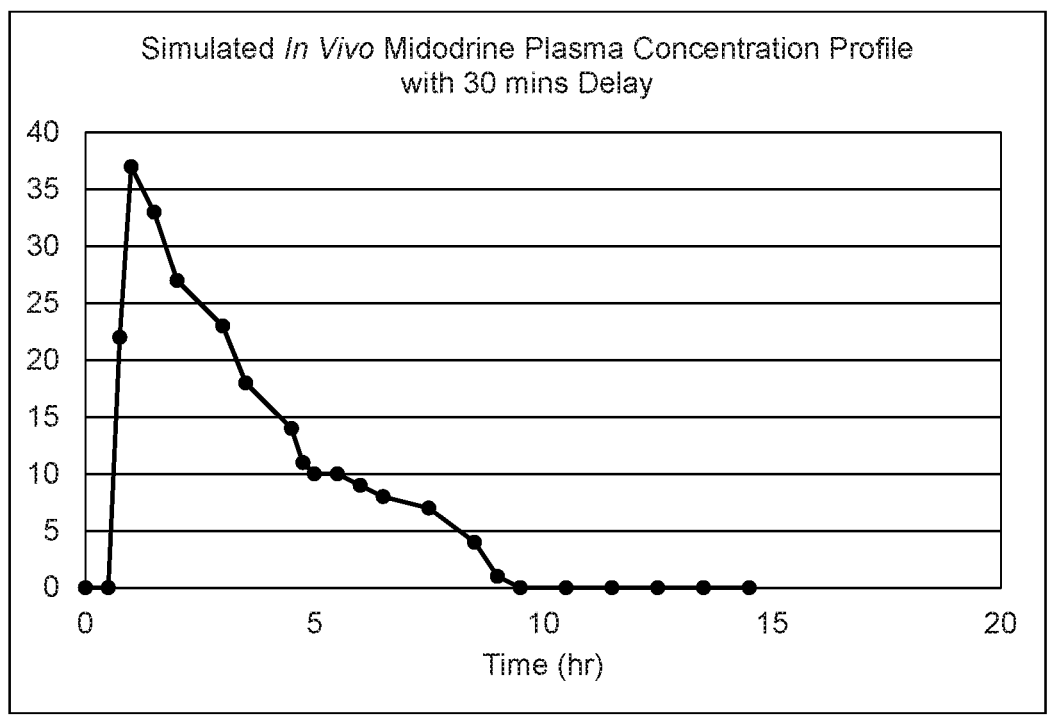
FIG. 8 is a graph of a simulated in vivo release profile of a delayed release period of about 30 minutes followed by an extended release period of about 10 hours.
Figure 9:
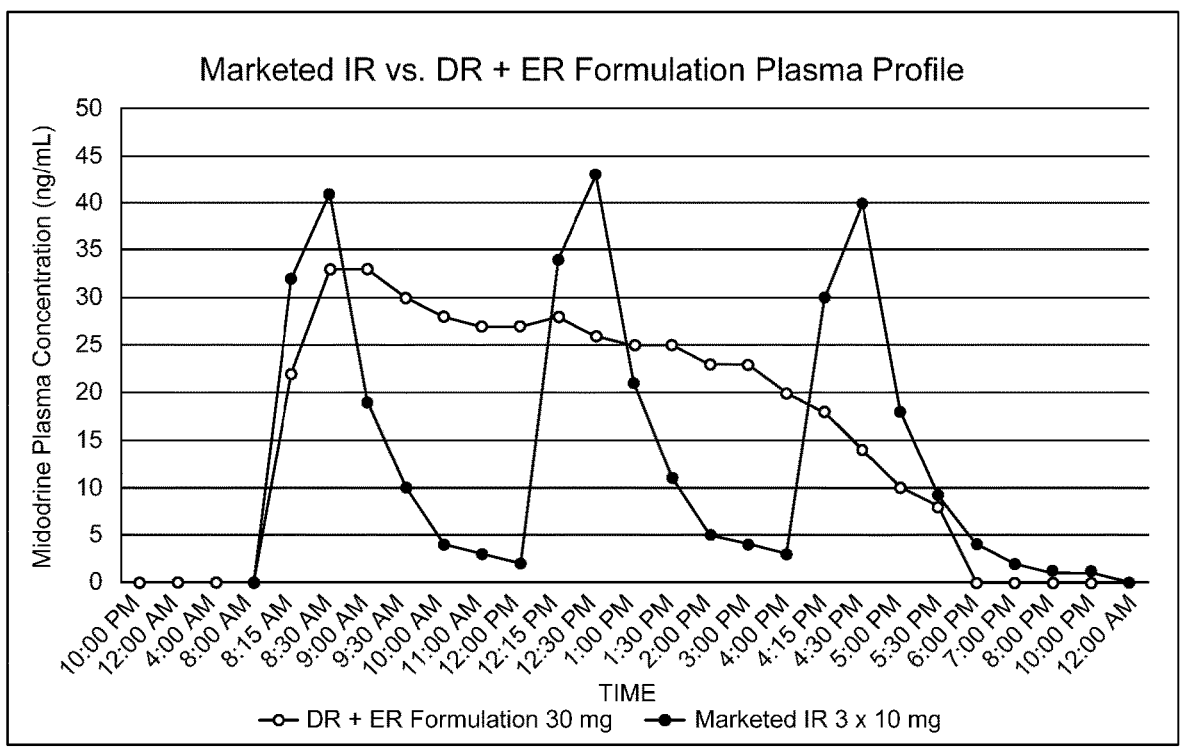
FIG. 9 is a graph of simulated in vivo release profiles of a marketed immediate release formulation in comparison with an exemplary formulation with a delayed release period of about 10 hours followed by an extended release period of about 10 hours.
Figure 10:
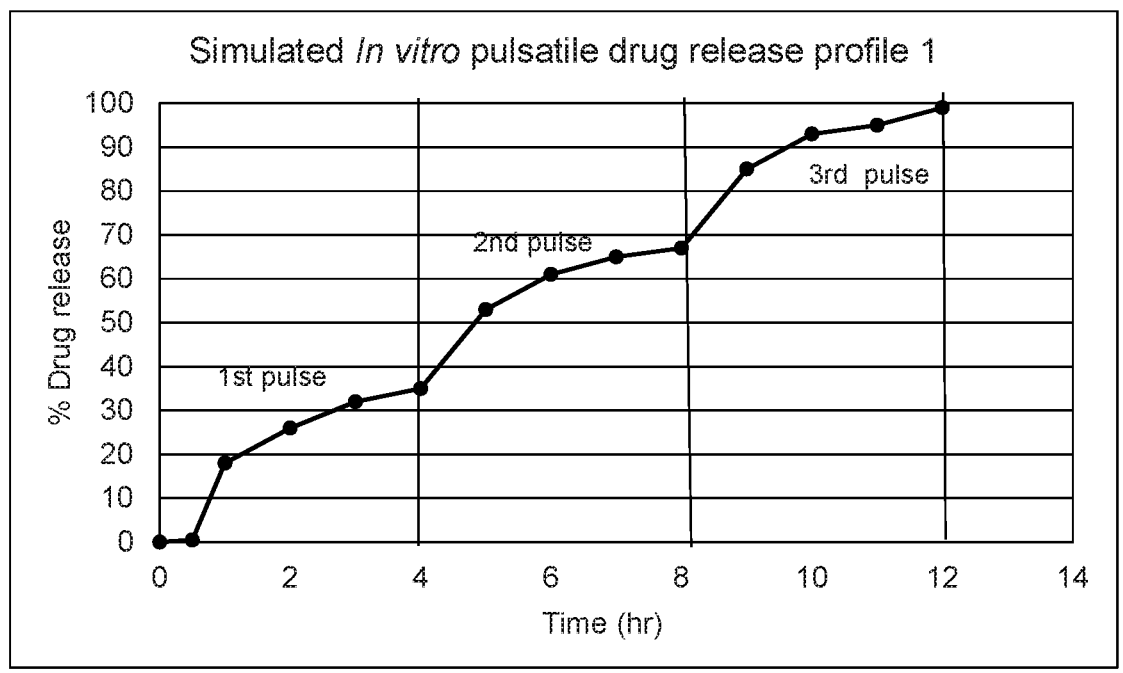
FIG. 10 is a graph of simulated in vitro pulsatile drug release profile with an equal amount of the drug released during each pulse (i.e. totally 10 mg/pulse).

Multi-particulate based drug delivery systems can also incorporate an immediate release component in the formulation. The drug, a filler and a binder are mixed in a higher shear granulator for a few minutes. A proper amount of water is sprayed onto the materials and wet mass is formed, which is then extruded on a twin-screw extruder. Extrudates obtained are then fed into a spheronizer where wet spherical pellets are produced and then dried in a fluid bed processor. These pellets can be split into two portions. One portion can be used as the immediate release component; the other portion can be further coated with a release controlling agent to form the extended release component. Both components are coated with delayed release coating separately. These two components can be filled into capsules, or blended with other excipients and compressed into orally disintegrated tablets, or mixed with a suspending vehicle to form a suspension. An example of the formulation is shown in Table 28 and the expected in vitro dissolution profile is shown in FIG. 7.

TABLE 28

| # | Ingredients | Quantity (mg) |
|---|---|---|
| | Immediate release multi-particulates | |
| 1 | Midodrine HCL | 12 mg |
| 2 | Microcrystalline cellulose | 20 mg |
| 3 | Polyvinyl pyrrolidine | 1.2 mg |
| 4 | Purified water | q.s. |

TABLE 28-continued

| # | Ingredients | Quantity (mg) |
|---|---|---|
| | Extended release multi-particulates | |
| 5 | Midodrine HCL | 18 mg |
| 6 | Microcrystalline cellulose | 30 mg |
| 7 | Polyvinyl pyrrolidine | 1.8 mg |
| 8 | Polyvinyl acetate | 10 mg |
| 9 | Triethyl citrate | 1 mg |
| 10 | Talc | 2 mg |
| 11 | Purified water | q.s. |
| | Delayed release coating | |
| 12 | Hypromellose | 14.0 mg |
| 13 | Ethyl cellulose (as dispersion) | 56.0 mg |
| 14 | Purified water | q.s. |
| | Total | 166 mg |

Example 16

Delayed and Extended Release Formulation with Pulsatile Drug Release

Extended release pellets can be prepared by extrusion, spheronization method.

The active agent, a filler, a rate controlling agent, and optionally a binder, are blended in a high shear granulator. A solvent is sprayed onto the blend and wet mass is formed. The wet mass is extruded, spheronized and dried to form spherical pellets. These extended release matrix pellets are then split into three parts, pellets I are coated with a 30 min delay release coating, e.g. SURELEASE dispersion and OPADRY. Pellets II are coated with a pH independent water insoluble coating that will not release any drug until 4 hours later. Pellets III can be coated with the same water insoluble coating at a higher level that will not release any drug until 8 hours later.

Figure 11:
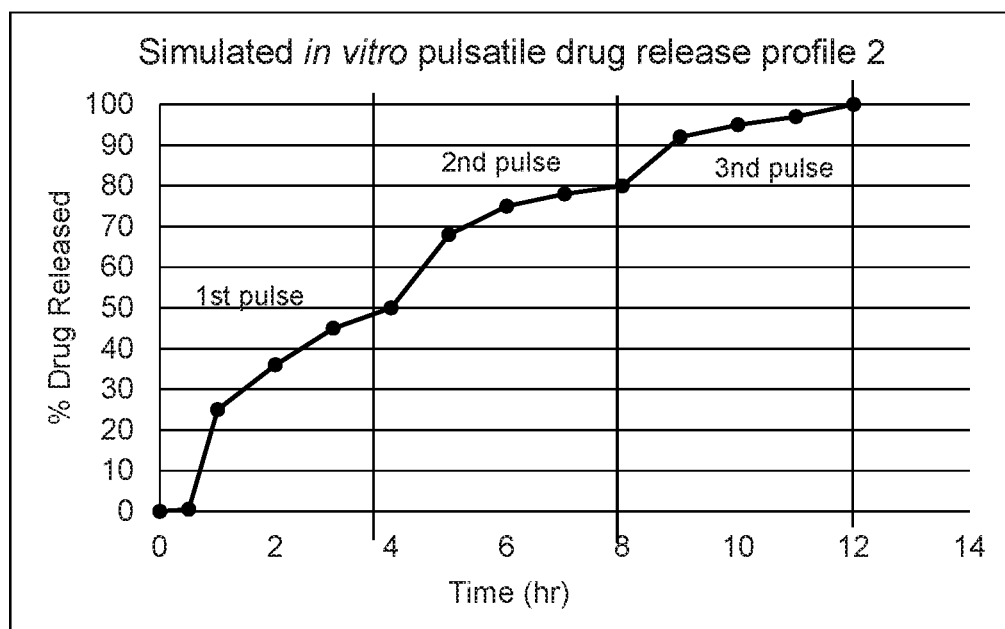
FIG. 11 is a simulated in vitro pulsatile drug release profile with different amounts of the drug released during each pulse (i.e. 15 mg/$1^{st}$ pulse, 9 mg/$2^{nd}$ pulse, 6 mg/$3^{rd}$ pulse).

Pulsatile drug release formulations can release an equal amount of the active agent during each pulse (see Table 29 & FIG. 10), or can release a different amount of the active agent during each pulse (see Table 20 & FIG. 11). Pulsatile drug release formulations can release the active agent for the same or different extended periods during each pulse.

TABLE 29

| # | Ingredients | Quantity (mg) |
|---|---|---|
| Pellets I (1$^{st}$ pulse) | Midodrine HCL | 10 mg |
| | Hypromellose | 50 mg |
| | Microcrystalline cellulose | 30 mg |
| | Polyvinyl porrolidine | 5 mg |
| | Opadry | 2.8 mg |
| | Surelease dispersion | 11.2 mg |
| | Purified water | q.s. |
| Pellets II (2$^{nd}$ pulse) | Midodrine HCl | 10 mg |
| | Hypromellose | 50 mg |
| | Microcrystalline cellulose | 30 mg |
| | Eudragit NE 30D | 18 mg |
| Pellets III (3$^{rd}$ pulse) | Midodrine HCl | 10 mg |
| | Hypromellose | 50 mg |
| | Microcrystalline cellulose | 30 mg |
| | Eudragit NE 30D | 32 mg |
| Total | | 339 mg |

TABLE 30

| # | Ingredients | Quantity (mg) |
|---|---|---|
| Pellets I (1$^{st}$ pulse) | Midodrine HCL | 15 mg |
| | Hypromellose | 75 mg |
| | Microcrystalline cellulose | 50 mg |
| | Polyvinyl porrolidine | 8 mg |
| | Opadry | 2.8 mg |
| | Surelease dispersion | 11.2 mg |
| | Purified water | q.s. |
| Pellets II (2$^{nd}$ pulse) | Midodrine HCl | 9 mg |
| | Hypromellose | 45 mg |
| | Microcrystalline cellulose | 27 mg |
| | Eudragit NE 30D | 18 mg |
| Pellets III (3$^{rd}$ pulse) | Midodrine HCl | 6 mg |
| | Hypromellose | 30 mg |
| | Microcrystalline cellulose | 20 mg |
| | Eudragit NE 30D | 32 mg |
| Total | | 349 mg |

What is claimed is:

1. A pharmaceutical composition comprising an effective amount of an active agent selected from midodrine, a pharmaceutically acceptable salt of midodrine, desglymidodrine, or a pharmaceutically acceptable salt of desglymidodrine; wherein the pharmaceutical composition is adapted to release the active agent in such a manner that there is not a fast peak plasma concentration of desglymidodrine; and
   wherein release of the active agent is delayed for from about 1 hour to about 12 hours.

2. The pharmaceutical composition of claim 1 further comprising an effective amount of a barrier coating agent to provide for a lag time of the active agent and optionally a rate controlling agent.

3. A pharmaceutical composition comprising an effective amount of an active agent selected from midodrine, a pharmaceutically acceptable salt of midodrine, desglymidodrine, or a pharmaceutically acceptable salt of desglymidodrine; wherein the pharmaceutical composition may be administered to a human subject in a supine position; and
   wherein release of the active agent is delayed for from about 1 hour to about 12 hours.

4. The pharmaceutical composition of claim 2, wherein the barrier coating agent is selected from an acid-insoluble coating agent, a water-insoluble coating agent, a water permeable coating agent, a water impermeable coating agent, a water soluble coating agent, and any combination thereof.

5. The pharmaceutical composition of claim 1, comprising a rate controlling agent, wherein the rate controlling agent is a water-soluble excipient, a water-insoluble excipient, a water impermeable excipient, and/or a water-permeable excipient.

6. The pharmaceutical composition of claim 1, further comprising a rate controlling agent, wherein the release of the active agent is extended for about 4 hours to about 14 hours.

7. The pharmaceutical composition of claim 1, wherein the pharmaceutical composition is in the form of an extended release tablet, a multiparticulate drug delivery, an oral suspension, a powder for oral suspension, a granule for oral suspension, a tablet for oral suspension, a gastroretentive drug delivery system, or any combination thereof; and
   wherein the pharmaceutical composition can be administered to a subject in a supine position.

8. The pharmaceutical composition of claim 1, comprising the active agent from about 4 mg to about 150 mg.

9. The pharmaceutical composition of claim 1, wherein the active agent provides a plasma level of desglymidodrine in a subject of at least about 3 ng/mL for a duration of at least about 4 hours.

10. The pharmaceutical composition of claim 1, wherein release of the active agent is delayed for about 10 hours.

11. The pharmaceutical composition of claim 1, wherein no more than 10%, optionally no more than 5% of the active agent is released in the first 10 hours.

12. A pharmaceutical composition comprising:
   (a) a delayed release composition comprising a delayed release agent; and
   (b) an extended release composition comprising (i) an effective amount of an active agent selected from midodrine, a pharmaceutically acceptable salt of midodrine, desglymidodrine, a pharmaceutically acceptable salt of desglymidodrine, or a combination thereof, and (ii) a rate controlling agent;
   wherein the pharmaceutical composition provides a delayed release period of from about 1 hour to about 12 hours, optionally, about 8 hours to about 12 hours, after administration to a subject, or wherein the pharmaceutical composition provides a delayed release period of about 1 hour to about 12 hours in an in vitro dissolution test with USP I (Basket) at 100 rpm in 900 mL of 0.1 N HCl at 37° C.

13. The pharmaceutical composition of claim 12, wherein the extended release composition comprises an extended release coating comprising the active agent and the rate controlling agent; and
   wherein the extended release composition is present in a percentage of the pharmaceutical composition of between about 5% (w/w) to about 95% (w/w), or optionally between about 30% (w/w) to about 80% (w/w).

14. The pharmaceutical composition of claim 12, wherein the extended release composition comprises an extended release matrix comprising the active agent and the rate controlling agent.

15. The pharmaceutical composition of claim 12, wherein the delayed release composition comprises a delayed release coating.

16. A method of treating a subject in need thereof, comprising administering to the subject a single dose of the pharmaceutical composition of claim 1, wherein the subject has a disorder comprising at least one of: orthostatic hypertension; postural orthostatic tachycardia syndrome (POTS); dysautonomia; symptoms of chronic orthostatic hypotension corresponding to autonomic failure associated with Bradbury-Eggleston syndrome, Shy-Drager syndrome, diabetes mellitus disease, and Parkinson's disease; and retrograde ejaculation.

17. A method of treating orthostatic hypotension (OH) in a subject in need thereof, comprising administering to the subject a single dose of the pharmaceutical composition of claim 1.

18. A method for treating or reducing the incidence of supine hypertension in a subject in need thereof, comprising administering to the subject a single dose of the pharmaceutical composition of claim 1.

19. The method of claim 16, wherein the pharmaceutical composition is an oral suspension and the dosage can be titrated to an effective level for the subject.

20. The method of claim 16, wherein the pharmaceutical composition is administered before the subject's normal sleep at night; and wherein the pharmaceutical composition has a delayed release period that overlaps with the subject's normal period of sleep or overlaps with the subject's period of being in a supine position.

* * * * *